(12) United States Patent
Slininger et al.

(10) Patent No.: US 10,982,185 B2
(45) Date of Patent: Apr. 20, 2021

(54) DESICCATION RESISTANT PSEUDOMONAD STRAINS AND TREATMENT OF AGRICULTURAL MALADIES THEREWITH

(71) Applicant: The United States of America, as represented by the Secretary of Agriculture, Washington, DC (US)

(72) Inventors: Patricia J. Slininger, Metamora, IL (US); David A. Schisler, Morton, IL (US); Maureen A. Shea Andersh, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 154 days.

(21) Appl. No.: 16/142,745

(22) Filed: Sep. 26, 2018

(65) Prior Publication Data
US 2020/0095537 A1 Mar. 26, 2020

(51) Int. Cl.
C12N 1/20 (2006.01)
C12R 1/39 (2006.01)
A01N 63/10 (2020.01)

(52) U.S. Cl.
CPC ............... *C12N 1/20* (2013.01); *C12R 1/39* (2013.01); *A01N 63/10* (2020.01)

(58) Field of Classification Search
CPC .................................................... A01N 63/10
See application file for complete search history.

(56) References Cited

U.S. PATENT DOCUMENTS

| | | | |
|---|---|---|---|
| 5,728,574 | A | 3/1998 | Legg |
| 6,107,247 | A | 8/2000 | Slininger et al. |
| 6,156,560 | A | 12/2000 | Chun |
| 6,277,625 | B1 | 8/2001 | Huang et al. |
| 9,297,027 | B1 | 3/2016 | Slininger et al. |
| 2011/0077158 | A1 | 3/2011 | Slininger et al. |

OTHER PUBLICATIONS

Azevedo M-M. et al., 2015, "Genesis of Azole Antifungal Resistance from Agriculture to Clinical Settings" J. Agr. Food Chem. 63(34): 7463-7468.
Berns, A.E., et al., 2008, "Effect of gamma-sterilization and autoclaving on soilorganic matter structure as studied by solid state NMR,UV and fluorescence spectroscopy," Eur. J. Soil Sci. 59: 540-550.
Boyd, A. E.W., 1972,"Potato storage diseases," Rev. Plant Path. 51: 297-321.
Burkhead, K. D., et al., 1995, "Bioautography Shows Antibiotic Production by Soil Bacterial Isolates Antagonistic to Fungal Dry Rot of Potatoes," Soil Biol. Biochem. 27(12): 1611-1616.
Crowe, J. H., et al., 1987, "Stabilization of dry phospholipid bilayers and proteins by sugars," Biochem. J. 242: 1-10.
Crowe, J. H., et al., 1988, "Interactions of Sugars with Membranes," Biochim. Biophys. Acta 947: 367-384.
Razavi darbar S. and Lakzian A., 2007, "Evaluation of Chemical and Biological Consequences of Soil Sterilization Methods," Caspian J. Env. Sci. 5(2): 87-91.
Desjardins A.E. and R.D. Plattner,1989, "Trichothecene toxin production by strains of Gibberella pulicaris (Fusarium sambucinum) in liquid culture and in potato tubers," J. Agric. Food Chem. 37: 388-392.
Desjardins, A. E., et al., 1993, "Population Structure and Genetic Analysis of Field Resistance in Thabendazole in Gibberella pullcaris from Potato Tubers," Phytopathology 83: 164-170.
European Center for Disease Prevention and Control, ECDC Technical Report: Risk assessment on the impact of environmental usage of triazoles on the development and spread of resistance to medical triazoles in Aspergillus species. ECDC, 2013.
Hanson, L. E., et al., 1996, "Sensitivity to Thiabendazole in Fusarium Species Associated with Dry Rot of Potato," Phytopathology 86: 378-384.
Kano R. et al., 2015, "Does Farm Fungicide use Induce Azole Resistance in Aspergillus fumigatus?," Med. Mycol. 53(2): 174-177.
Kawchuk, L. M., et al., 1994, "Resistance to Thiabendazole and Thiophanate-Methyl in Canadian Isolates of Fusarium Sambucinum and Helminthosporium Solani," Am. Potato J. 71: 185-192.
Schisler D.A. & Slininger P.J., 1994, Selection and Performance of Bacterial Strains for Biologically Controlling Fusarium Dry Rot of Potatoes Incited by Gibberella pulicaris, Plant Dis. 78: 251-255.
Schisler D. A. et al., 2009, "Bacterial Antagonists, Zoospore Inoculum Retention Time and Potato Cultivar Influence Pink Rot Disease Development," Am. J. Potato Res. 86(2): 102-111.
Schisler D.A., et al., 2016, "Appraisal of Selected Osmoprotectants and Carriers for Folmulating Gram-negative Biocontrol Agents Active Aggainst Fusarium Dry Rot on Potatoes in Storage," Biological Control 98:1-10.
Slininger, P. J. et al. (1994). Proceedings of the Third International Workshop on Plant Growth-Promoting Rhizobacteria (pp. 29-32). Adelaide, South Australia: CSIRO.
Slininger P.J. et al., 2003, "Postharvest Biological Control of Potato Sprouting by Fusarium Dry Rot Suppressive Bacteria," Biocontrol Sci. Tech. 13(5): 477-494.
Slininger P. J. et al., 2007, "Biological control of post-harvest late blight of potatoes," Biocontrol Sci. Tech. 17(6): 647-663.
Slininger P.J. et al., 2010, "Polysaccharide production benefits dry storage survival of the biocontrol agent Pseudomonas fluorescens S11:P:12 effective against several maladies of stored potatoes," Biocontrol Sci. Tech. 20(3): 227-244.
Slininger, P. J. et al., 2010, Multi-strain co-cultures surpass blends for broad spectrum biological control of maladies of potatoes in storage, Biocontrol Sci. Technol. 20(8): 763-786.

(Continued)

*Primary Examiner* — Bin Shen
(74) *Attorney, Agent, or Firm* — John Fado; Maria Restrepo-Hartwig

(57) ABSTRACT

Novel strains of *Pseudomonas fluorescens* are disclosed. Several novel mutated strains of Pseudomonads are engineered by repetitive culturing of a parent strain under stressed conditions. Various enriched populations are screened and ranked based on relative performance indices including viable cell yield during growth, efficacy in suppression of dry rot disease, cell growth recovery after dry storage and resistance to switchgrass hydrolysate.

19 Claims, 10 Drawing Sheets

Specification includes a Sequence Listing.

(56) References Cited

OTHER PUBLICATIONS

Slininger, P. J. & Schisler, D. A. (2011). Fungicides for Plant and Animal Diseases (pp. 141-166). Rijeka, Croatia: InTech).
Slininger, P.J. & Schisler, D.A, 2013, "High-Throughput Assay for Optimising Microbial Biological Control Agent Production and Delivery," Biocontrol Sci. Tech. 23: 920-943.
Slininger P.J., et al., 2015, "Evolved strains of Scheffersomyces stipitis achieving high ethanol productivity on acid- and base-pretreated biomass hydrolyzate at high solids loading," Biotechnol. Biofuels. 8(60): 1-27.
Slininger P.J., et al., 2016, "Comparative Lipid Production by Oleaginous Yeasts in Hydrolyzates of Lignocellulosic Biomass and Process Strategy for High Titers," Biotechnol. Bioeng. 113:1676-1690.
Spadaro, D., et al., 2010, "Effect of Culture Age, Protectants, and Initial Cell Concentration on Viability of Freeze-Dried Cells of Metschnikowia pulcherrima," Can. J. Microbiol. 56(10): 809-815.
Yanez-Mendizabal, V., et al., 2012, "Endospore Production Allows Using Spray-Drying as a Possible Formulation System of the Biocontrol Agent Bacillus subtilis CPA-8," Biotechnol. Lett. 34(4): 729-735.
Yanez-Mendizabal, V., et al., 2102, "Formulation Development of the Biocontrol Agent Bacillus subtilis Strain CPA-8 by Spray-Drying," J. Appl. Microbiol. 112(5): 954-965.
International search report on PCT/US2019/052559.

DESICCATION RESISTANT PSEUDOMONAD STRAINS AND TREATMENT OF AGRICULTURAL MALADIES THEREWITH

FIELD OF THE INVENTION

The present invention relates generally to novel strains of Pseudomonads that are tolerant of long-term storage under desiccated conditions and the use of such strains as biological control agents for fungal agricultural diseases. More particularly, this invention relates to novel strains of *Pseudomonas fluorescens* prepared through engineered mutagenesis that are effective antagonists against *Fusarium* species responsible for agricultural diseases that occur in the field or in postharvest storage.

BACKGROUND OF THE INVENTION

There is growing evidence that widespread use of chemical-based microbial control products, such as azole compounds, to control fungal diseases and other problems in plants and animals has led to chemical resistance of such plant pathogens and medically important fungi (see e.g., Azevedo et al. (2015) *Journal of Agricultural and Food Chemistry,* 63 (34), 7463-7468; Kano et al. (2015) *Medical Mycology,* 53, 174-177). While many fungicides appear not to pose a threat to humans through resistance, azole-based fungicides do appear harmful. Azole-based therapies are arguably the most important class of oral drugs humans use to fight the infections caused by, for example, fungi in the *Aspergillus* genus. An increase in azole-resistant infections is likely to worsen what is already a significant human health impact (see e.g., European Center for Disease Prevention and Control, ECDC Technical Report: Risk assessment on the impact of environmental usage of triazoles on the development and spread of resistance to medical triazoles in *Aspergillus* species. ECDC, 2013).

To combat this detrimental issue, microbial products commonly referred to as "biological control agents" (BCAs) are being developed. BCAs may be mass produced for field applications and are most economically and conveniently stored in a stable dormant dry state prior to sales and application. Pseudomonads (e.g., *Pseudomonas fluorescens* strains and other *Pseudomonas* spp.) are known to be effective BCAs of field and postharvest potato diseases (e.g., *Fusarium* dry rot, late blight, pink rot, among others) and have also been reported to reduce sprouting of potatoes in storage (see e.g., Schisler, D. A. & Slininger, P. J. (1994). *Plant Disease,* 78, 251-255; Slininger, P. J. et al. (2003). *Biocontrol Science and Technology,* 13(5), 477-494; Slininger, P. J. et al. (2007). *Biocontrol Science and Technology,* 17(5/6), 647-663; Schisler, D. A., Slininger, P. J., Miller, J. S., Woodell, L. K., Clayson, S., & Olsen, N. (2009). *American Journal of Potato Research,* 86, 102-111; Slininger, P. J. et al. (2010). *Biocontrol Science and Technology,* 20(3), 227-244; Slininger, P. J. & Schisler, D. A. (2011). *Fungicides for Plant and Animal Diseases* (pp. 141-166). Rijeka, Croatia: InTech). Due to processing demands, a majority of the annual potato harvest is generally stored at lower temperatures (e.g., 7° C. to 13° C.) above that needed for ideal sprout control (ASAE, 1990. Design and management of storages for bulk, fall-crop Irish potatoes. St. Joseph, Mich.: ASAE). Consequently, chemical sprout inhibitors are applied to a majority of the potato harvest to extend storage time (see e.g., Lewis, M. D., et al. (1996) *Potato Grower* 25(9): 8-9); Slininger, P. J. et al. (2003); Slininger et al. (2010); Slininger, P. J. & Schisler, D. A. (2011)).

Though potentially effective as BCAs, Pseudomonads are difficult to economically produce and deliver on a commercial scale because they are Gram-negative non-spore-forming bacteria with no cell wall, making them among the least resilient of microorganisms, especially under desiccated storage conditions. Numerous strains of this genus have been isolated from agricultural ecosystems, and in many cases, biological control functions have been observed and studied at the molecular level. As such, much of their potential remains untapped and could be useful for applications benefiting from BCAs. A commercial example of potential BCA use is in potato production and processing to control various crop diseases. It is well known that potatoes are one of the most important sources of human food globally. Disease reduction has been attempted using a combination of approaches including resistant varieties (e.g., discovered or developed via genetic modification or selective crossing), chemicals, crop management, and biological control agents.

Of the disease problems which impact the commercial potato industry, fungal dry rot causes greater losses in storage and transit of both seed and commercial potatoes than any other postharvest disease (see e.g., Secor and Salas (2001), *Fusarium* dry rot and *Fusarium* wilt. In Compendium of Potato Diseases ($2^{nd}$ Edition), W. R. Stevenson, et al. (Editors), APS Press: St. Paul Minn.). Several species of the fungal *Fusaria* genus are known to induce this disease. For example, *Gibberella pulicaris* (Fries) Sacc. (anamorph: *Fusarium sambucinum* Fuckel) is a major causative fungal species worldwide, especially in North America (see e.g., Boyd, A. E. W. (1972). Potato storage diseases. *Reviews of Plant Pathology* 51: 297-321). *Fusarium* spp. can survive for years in field soil, but the primary inoculum is generally borne on seed tuber surfaces. These dry rot-inducing fungi typically infect potatoes via wounds in the periderm inflicted during harvesting or subsequent handling. In stored potatoes, for instance, dry rot normally develops most rapidly in high relative humidity (e.g., 70% and higher) and at temperatures ranging from about 15° C. to 20° C. but continues to advance at other temperatures as well. Although rots caused by *Fusarium* spp. seldom reach epidemic proportions, the level of infected tubers in storage often reaches 60% or higher, with average losses estimated in the 10% to 20% range (see Secor and Salas (2001)). In addition to destroying tissue, *Fusarium* spp. can produce trichothecenes that have been implicated in mycotoxicoses of both humans and animals (see e.g., A. E. Desjardins and R. D. Plattner (1989) Trichothecene toxin production by strains of *Gibberella pulicaris* (*Fusarium sambucinum*) in liquid culture and in potato tubers. *J. Agric. Food Chem.* 37: 388-392).

Chemical control of causative fungi is no longer a practical or effective solution against its target diseases due to the occurrence of widespread resistance to chemical treatments normally used on food-grade potatoes (e.g., azoles such as thiabendazole, imidazoles, triazoles, tebuconazole, fluconazole). The narrow mode of action of azoles results in a relatively easy path for fungal organisms to develop resistance to multiple azole moieties even from exposure to just one type (see Azevedo et al. 2015). It is believed that over 80% of naturally-occurring *Fusarium sambucinum* strains, causative of potato dry rot, have developed resistance to TBZ, and available treatment options are limited, especially in postharvest potatoes destined for food use (see e.g., Desjardins, A. E., et al. (1993) *Phytopathology* 83: 164-170; Hanson, L. E., et al. (1996) *Phytopathology* 86: 378-384; Kawchuk, L. M., et al. (1994) *Am. Potato J.* 71: 185-192). In addition, to prevent loss of effectiveness of medically important antifungal antibiotics for human applications, there is growing pressure to move away from azole use in agriculture. To find alternatives to this currently ineffective and undesirable azole chemistry, eighteen strains of *Pseudomonas* antagonistic to *F. sambucinum* were discovered in soil and periderm samples from fields showing low incidence of dry rot (see e.g., Schisler, D. A. & Slininger, P. J. (1994). *Plant Disease,* 78, 251-255). Three of these bacterial strains (referred to as S11P12, P22Y05, and S22T04) were ranked to have greatest commercial promise due to their ease of efficient, high yielding cultivation in liquid culture (a U.S. industry standard) while still retaining biocontrol efficacy (see e.g., Slininger, P. J. et al. (1994). *Proceedings of the Third International Workshop on Plant Growth-Promoting Rhizobacteria* (pp. 29-32). Adelaide, South Australia: CSIRO). Additionally, compared to mixtures of three pure cultures, a one vessel three-strain coculture was consistently more efficacious against fungal diseases and sprouting, a feature that makes the application of multiple bacterial strains in one treatment more economically tractable (see e.g., Slininger, P. J. et al. (2010). *Biocontrol Science and Technology,* 20(8), 763-786). However, there still remains a significant hurdle to the widespread commercial use of *Pseudomonas* strains due to the inability to effectively and economically store viable cultures for extended periods.

There thus exists an ongoing industrial need to develop genetically improved strains of *Pseudomonas* that are resilient to extended desiccated storage periods. There is a particular need to develop such strains that are resilient to long-term desiccated storage and can retain viability for agricultural use as biological control agents.

SUMMARY OF THE INVENTION

To address these challenging issues for the development of resilient Pseudomonad strains, the present invention accordingly provides novel microbial strains that are resilient to long-term dry storage as well as methods of using the novel strains for the prevention and treatment of maladies affecting agricultural products. Parent strains of *P. fluorescens* are subjected to selective pressure environments to strategically engineer mutagenesis in those strains to result in novel strains with enhanced capabilities of withstanding dry, desiccated, long-term storage conditions as compared to the parent strains while still maintaining desired functionality and characteristics to be used as BCAs in agricultural applications.

In an aspect the invention is a novel microbial strain produced from a parent strain of *P. fluorescens*. The novel strain is selected from the group consisting of: ARS Culture Collection Patent Deposit Accession Numbers NRRL B-67667; NRRL B-67668; NRRL B-67669; NRRL B-67670; NRRL B-67671; NRRL B-67672; NRRL B-67673; NRRL B-67674; NRRL B-67675; a microbial cell line having all of the identifying characteristics of any of the foregoing; and combinations or cocultures thereof. In a related aspect, the invention includes methods of producing a novel microbial strain having enhanced capability and tolerance to withstand long-term, partially or fully desiccated storage while maintaining growth and bioefficacy phenotypes when rehydrated. The method includes subjecting a parent strain of interest to a process of engineered mutagenesis to produce the novel microbial strain having desirable identifying characteristics while maintaining functionality as anti-fungal BCA. In a further aspect, the invention is a method of treating agricultural products with a biological control agent comprising a novel strain of selected from the group consisting of: ARS Culture Collection Patent Deposit Accession Numbers NRRL B-67667; NRRL B-67668; NRRL B-67669; NRRL B-67670; NRRL B-67671; NRRL B-67672; NRRL B-67673; NRRL B-67674; NRRL B-67675; a microbial cell line having all of the identifying characteristics of any of the foregoing; and combinations or cocultures thereof.

In a further aspect, the invention is a method of generating a novel microbial strain. The method includes (a) culturing a parent strain of the novel microbial strain in a first medium for a time sufficient to achieve a predetermined culture density and create a base culture; (b) passaging the base culture by drawing one or more samples from the base culture to create at least one passaged sample; (c) optionally pelletizing the at least one passaged sample and suspending each passaged sample separately in a second medium to create a series of passaged samples; (d) subjecting the series of passaged samples to at least one stress condition to create a series of stressed samples; (e) measuring at least one characteristic of the series of stressed samples to create at least one measured characteristic; and (f) determining whether the measured characteristic is superior to the same characteristic of the parent strain to select at least one novel mutant strain from the series of stressed samples.

It is an advantage of the present invention to provide novel strains of Pseudomonads that are resilient to long-term dry storage.

It is another advantage of the present invention to provide methods of producing novel microbial strains using engineered mutagenesis to create organisms having desirable user-defined characteristics.

It is a further advantage of the present invention to provide methods of preventing and treating various fungal infections in agricultural environments.

It is yet another advantage of the present invention to provide methods of preventing and treating potato maladies including *Fusarium* dry rot, late blight, pink rot, sprouting, among others.

An additional advantage of the invention is to provide broad spectrum microbial control agents as alternatives to antifungal compounds.

A further advantage of the present invention is to provide a kit for inoculating agricultural areas with novel BCA strains to control fungal populations.

Yet another advantage of the invention is to provide broad spectrum antifungal microbial alternatives produced as a coproduct of a renewable lignocellulose in a biorefinery.

This summary is provided to introduce a selection of concepts in a simplified form that are further described below in the detailed description. This summary is not intended to identify all key or essential features of the claimed subject matter, nor is it intended to limit the scope of the claimed subject matter.

BRIEF DESCRIPTION OF THE DRAWINGS

FIG. 1 illustrates a flow diagram as an embodiment for the engineered mutagenesis process herein described.

FIG. 2 shows a stacked bar graph for overall ranking of novel strains created via engineered mutagenesis of parent strain S22T04 reflected in the total of relative performance indices based on three evaluation factors of cell yield, dried droplet regrowth, and dry disease suppression.

FIG. 3 shows a stacked bar graph for overall ranking of novel strains created via engineered mutagenesis of parent strain P22Y05 reflected in the total of relative performance indices based on three evaluation factors of cell yield, dried droplet regrowth, and dry disease suppression.

STATEMENT OF DEPOSIT

Figure 1:
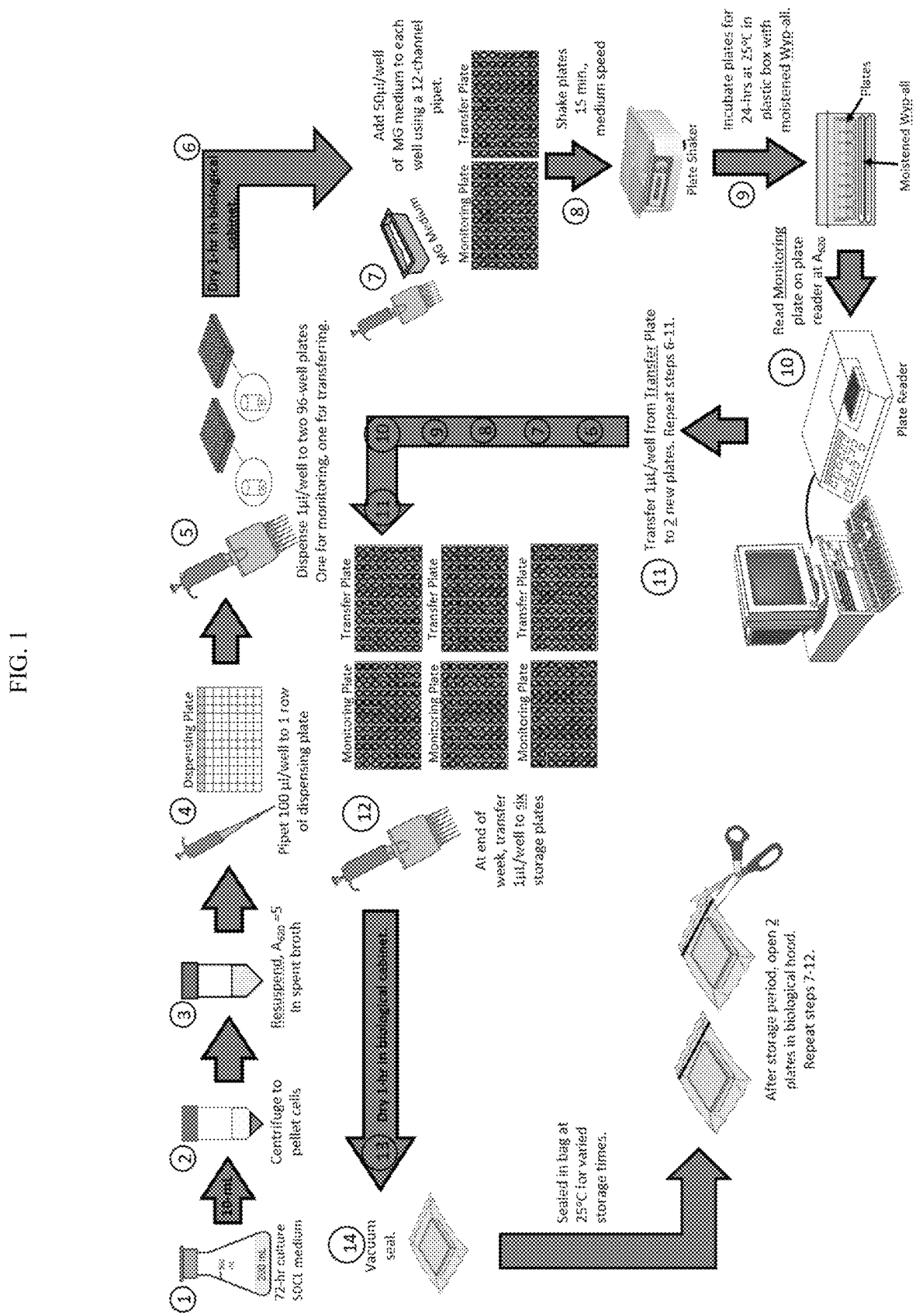
Figure 2:
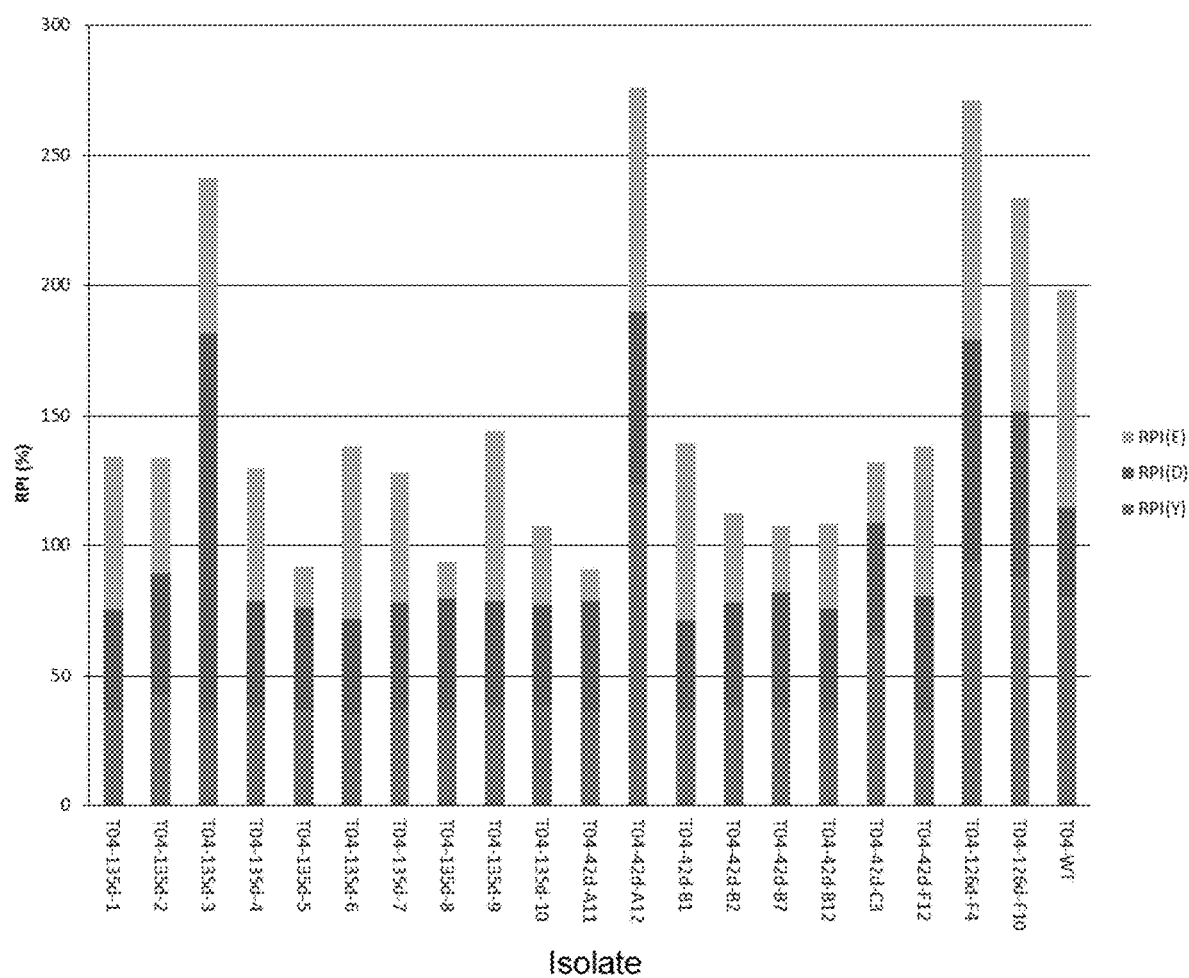
Figure 3:
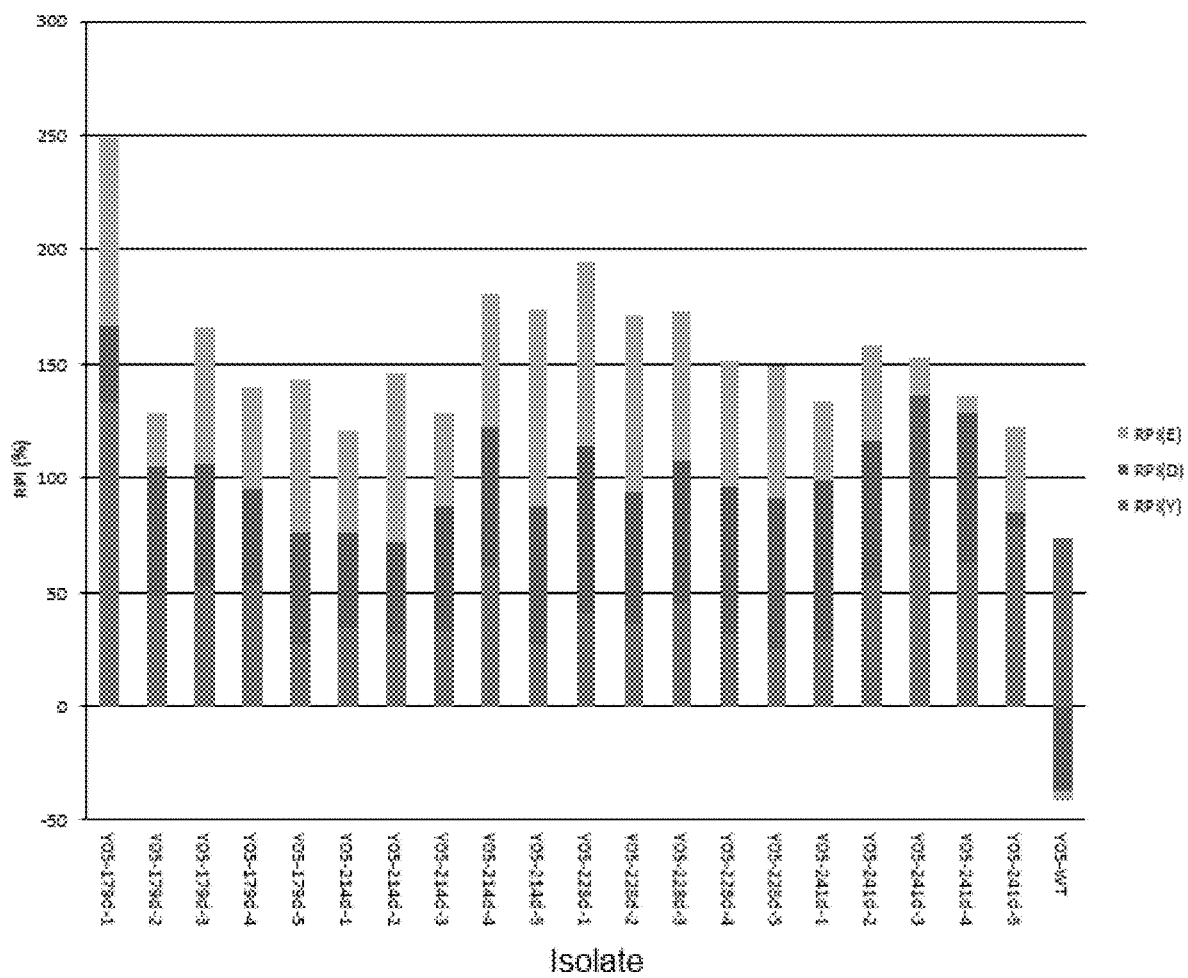
Figure 4:
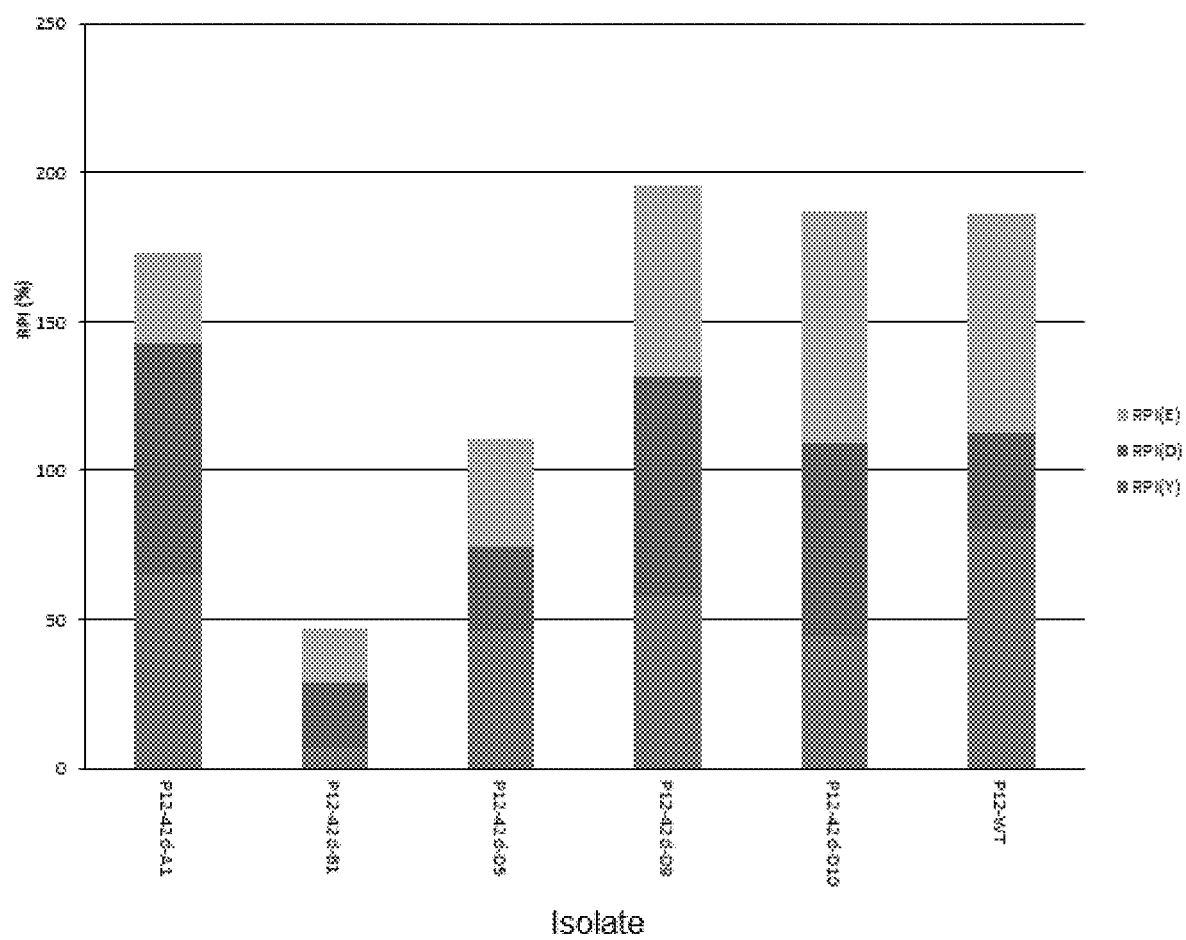
FIG. 4 shows a stacked bar graph for overall ranking of novel strains created via engineered mutagenesis of parent strain S11P12 reflected in the total of relative performance indices based on three evaluation factors of cell yield, dried droplet regrowth, and dry disease suppression.

Samples of the following novel microorganism strains shown in the Table 1 have been deposited with the U.S.D.A. Agricultural Research Service (ARS) Patent Culture Collection, National Center for Agricultural Utilization Research, 1815 N. University Street, Peoria, Ill. 61604, in a manner affording permanence of the deposit and ready accessibility thereto by the public if a patent is granted on the subject matter disclosed herein. Each of the strains shown in Table 1 were deposited on Aug. 16, 2018 and developed via engineered mutagenesis from the indicated Parent Strains.

TABLE 1

| Parent Strain | Isolate Designation | ARS Deposit Accession Number |
| --- | --- | --- |
| *P. fluorescens* S22:T:04 (NRRL B-21102) | T04-126d-F10 | NRRL B-67667 |
| *P. fluorescens* S22:T:04 (NRRL B-21102) | T04-42d-A12 | NRRL B-67668 |
| *P. fluorescens* S11:P:12 (NRRL B-21133) | P12-42d-D9 | NRRL B-67669 |
| *P. fluorescens* S22:T:04 (NRRL B-21102) | T04-126d-F4 | NRRL B-67670 |
| *P. fluorescens* S11:P:12 (NRRL B-21133) | P12-42d-A1 | NRRL B-67671 |
| *P. fluorescens* P22:Y:05 (NRRL B-21053) | Y05-179d-1 | NRRL B-67672 |
| *P. fluorescens* P22:Y:05 (NRRL B-21053) | Y05-228d-1 | NRRL B-67673 |
| *P. fluorescens* S11:P:12 (NRRL B-21133) | P12-42d-D10 | NRRL B-67674 |
| *P. fluorescens* P22:Y:05 (NRRL B-21053) | Y05-214d-4 | NRRL B-67675 |

These deposits have been made under the terms of the Budapest Treaty on the International Recognition of the Deposit of Microorganisms for the Purposes of Patent Procedure and the regulations thereunder. All restrictions on the availability to the public of these deposited microorganisms will be irrevocably removed upon issuance of a United States patent based on the present patent application. For the purposes of this invention, any strain having the identifying characteristics of the deposited strains and including subcultures and variants thereof which have the identifying characteristics and activity as described herein are included within the scope of the invention. The biological materials identified herein have been deposited under conditions such that access to the microorganisms are available during the pendency of the patent application to one determined by the Commissioner to be entitled thereto under 37 C.F.R. § 1.14 and 35 U.S.C § 122. The deposited biological material will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

The inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

SEQUENCE LISTING

The Sequence Listing submitted via EFS-Web as ASCII compliant text file format (.txt) and filed on Sep. 26, 2018, named "SequenceListing_ST25," (created on Sep. 26, 2018, 1 KB) is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

DETAILED DESCRIPTION OF THE INVENTION

Unless herein defined otherwise, all technical and scientific terms used herein generally have the same meaning as commonly understood by one of ordinary skill in the art to which this invention belongs. The definitions herein described may or may not be used in capitalized as well as singular or plural form herein and are intended to be used as a guide for one of ordinary skill in the art to make and use the invention and are not intended to limit the scope of the claimed invention. Mention of trade names or commercial products herein is solely for the purpose of providing specific information or examples and does not imply recommendation or endorsement of such products.

As used in the description of the invention and the appended claims, the singular forms "a," "an," and "the" are intended to include the plural forms as well, unless the context clearly indicates otherwise.

The term "agriculturally acceptable carrier" (or "carrier") includes any gaseous, liquid, or solid substrate, solvent, propellant, etc. used in the process of delivering the novel strains of the present invention which may serve to improve the selectivity, effectiveness, and/or safety of administration to which the novel strains of the present invention can be added and that is not harmful to the novel strains of the invention or the target to which it is being applied. The carrier can be combined with the novel strains of this invention and assists in the application of the novel strains to the soil or seed or plant or parts thereof so that the bacteria of this invention grow and colonize the target area. Non-limiting examples of agriculturally acceptable carriers include talc, starch, sucrose, lactose, and other carbohydrates, polysaccharides, milk/skim milk, cellulose, water, oil, any oil and water emulsion (e.g., an oil-in-water emulsion, an oil-in-water-in-oil emulsion, a water-in-oil emulsion, a water-in-oil-in-water emulsion, an emulsified cream containing oil and water), a buffered solution, aqueous monosorbitan oleate, Polysorbate 80 (polyoxyethylene sorbitan monooleate), Silwet L-77 (siloxane polyalkyleneoxide copolymer, also known as aqueous polyalkyleneoxide modified heptamethyltrisiloxane), other aqueous solutions containing emulsifier(s) and/or surfactant(s), methylcellulose, clay, sand, peat, vermiculite, diatomaceous earth, a cereal grain flour or meal, cotton meal, rice, seeds, plant seeds, and liquid or solid media. The oil can be any paraffinic oil that can be emulsified with water or any vegetable oil that can be emulsified with water or can be more of a solid (e.g., a wax, petroleum jelly, etc.). An agriculturally acceptable carrier can also be a polymer, such as polyvinyl alcohol (PVA), polyethylene glycol (PEG), polyacrylic acid (PAA), poly (lactic acid) (PLA), poly(glycolic acid) (PGA), copolymer of poly(lactic-co-glycolic acid) (PLGA), poly(ε-caprolactic acid) (PCLA), poly(β-hydroxybutyric acid), poly(β-hydroxyvaleric acid), polydioxanone, poly(ethylene oxide), poly(malic acid), poly(tartronic acid), polyphosphazene, polyethylene (PE), polystyrene (PS), agar (alginate) or other polysaccharides, gelatin, or combinations thereof. The carrier should be compatible with and not harm or kill the bacteria of the invention. The carrier may also release the bacteria of the invention into the soil after application to the soil or onto plants after application onto the plants in, for example, a delayed or controlled release fashion. Any carrier that permits the bacteria of the present invention to be delivered to the soil and/or target plant in a manner such that the bacteria remains viable may be employed in a composition comprising the bacteria so long as the carrier does not harm native plants and crops.

The term "BCA" or "biological control agent" means one or more microorganisms used independently, or in various combinations, or as part of a management program to control plant diseases caused by a variety of sources (e.g., fungi, bacteria, virus, etc.). The microorganism has the ability or functionality to reduce or eliminate the disease and/or the disease-causing source(s) and is sometimes referred to as an "antagonist" against the disease and/or disease-causing source of interest. For example, an agricultural product may be inoculated with an amount of one or more antagonists such as certain bacterial strain(s) to control growth of one or more disease-causing fungal strains.

The term "consisting essentially of" excludes additional method (or process) steps or composition components that substantially interfere with the intended activity of the method (or process) or composition and can be readily determined by those skilled in the art (for example, from a consideration of this specification or practice of the invention disclosed herein). This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms in alternative forms of the disclosed embodiments.

The term "engineered mutagenesis" refers to artificial laboratory methods that introduce one or more stress conditions with or without the application of additional mutagens (e.g., chemical, environment, etc.) to induce and selectively enrich for phenotypic changes of a parent strain (e.g., wild-type or other mutant strain) of an organism to achieve improvement and/or enhancement of at least one user-defined function and/or identifying characteristic (e.g., enhanced capability to withstand partially or fully desiccated storage, while maintaining growth and bioefficacy phenotypes when rehydrated; enhanced growth and bioefficacy phenotypes; resistance and tolerance to dry storage conditions for extended time periods; and combinations thereof) and create one or more mutagenized populations of organisms exhibiting the improved and/or enhanced user-defined function(s) and/or identifying characteristics. The stress conditions may also introduce favorable characteristics in a population by applying strategic enrichment techniques to select for desired phenotypic improvements. For example, repeated cycling of a population through growth, desiccation, rehydration, growth, etc. such that those isolates with phenotypes best enabling them to thrive will be enriched. The desired phenotype(s) may result from mutational changes and/or from epigenetic changes.

The term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it may not be possible to specify an exact "effective amount," though preferred ranges have been provided herein. An appropriate effective amount may be determined, however, by one of ordinary skill in the art using only routine experimentation.

The term "media" or "medium" as used herein refers to any suitable media for microbial cell cultivation. Media may include sources of some or all of the following types of ingredients (of appropriate purity) or included in complex supplements: yeast extract; peptone; casein hydrolysate; soy hydrolysate; corn steep; starch hydrolysate; lignocellulosic hydrolysate; macro and trace-elements and minerals; purines and pyrimidines; vitamins; nitrogen sources including amino acids, urea, ammonium, nitrate and others; carbon sources including sugars and sugar alcohols; or other suitable ingredients as determined by a skilled artisan. Such media selection would be subject to optimization or choice based on commercial economics and ingredient availability by those skilled in the art. In embodiments, media may include diverse sugars (including pentoses and others) and other organic compounds to yield antifungal BCAs from parent strains. For example, such sugars and compounds are often found in the waste or dilute sugar streams in the lignocellulose biorefining industry, allowing coproduction of BCAs alongside biofuel production.

The term "mutagenesis" according to the invention refers to the introduction via engineered mutagenesis of at least one alteration in a polynucleotide sequence, accessibility of the polynucleotide sequence for expression, and/or any expression-influencing (i.e., epigenetic) changes to the DNA, which results in an altered gene function or protein. Such an alteration according to the presently disclosed subject matter can involve substitution, insertion, or deletion introduced into any portion of a polynucleotide sequence and/or any factors (e.g., accessibility of the sequence for expression) that may impact genetic expression not necessarily involving changes to the polynucleotide sequence. An organism where such an alteration has occurred may be referred to as a "mutant" or "mutagenized" strain.

The term "novel strain" refers to a stable mutant strain of microorganism derived from engineered mutagenesis of a parent strain having changes in the DNA sequence or epigenetic changes which influence its availability for reading and expression, such that a stable strain having an altered heritable phenotype may result. Such a mutant strain may remain the same species as the parent strain or may be altered into another species according to taxonomic conventions. In embodiments, a novel strain may be isolated and essentially free of other strains or, alternatively, mixed or combined with other strains of the same or other species.

The term "parent strain" refers to a strain of microorganism that is any wild-type strain or a mutant strain and is used as a starting strain in the engineered mutagenesis scheme of the invention. For example, the *Pseudomonas fluorescens* strains (e.g., S11P12, P22Y05, and S22T04) referred to herein. It should be appreciated that the naming conventions provided herein are currently accurate but taxonomic changes may occur in *Pseudomonas* spp. identification due to ongoing genomic sequencing studies and taxonomic conventions. It is intended that the taxonomic terminology used herein will include any future changes to such terminology.

The term "optional" or "optionally" means that the subsequently described event or circumstance may or may not occur, and that the description includes instances in which said event or circumstance occurs and instances where it does not. For example, the phrase "optionally comprising a mutagen" means that a mutagen may or may not be present and that this description includes compositions that contain and do not contain a mutagen.

The term "relative performance indices" or "RPI" refers to a statistical ranking of a mutant strain relative to their respective parent strain using a variety of measured parameters. For example, these parameters may include viable cell yield during growth, efficacy in suppression of dry rot disease, and cell growth recovery after dry storage, among others such as viable cell fractions surviving drying and storage, or cell mass yield, or cell growth rate. Additionally, strain performance maybe ranked using the suggested parameters across a variety of production and application conditions (e.g., cultivation, formulation, drying, storage, rehydration conditions); or more expedient to commercial needs (see examples below) strains can be evaluated and ranked under one set of specific conditions deemed most amenable to feasible industrial production. Other ranking systems might also be devised and applied as discussed below, such as involving weighted parameters to prioritize ranking criteria based on economics or functional requirements in production or application. Other parameters could also be measured and used for ranking strains, such as for example, bacterial cell biomass accumulation, cell biomass yield per sugar supplied or used, percent viable cell mass accumulated, specific growth rate, sugar utilization rate, efficacy against other diseases or sprouting, and others as may be deemed appropriate.

The present invention addresses the need for novel microbial strains for use as BCAs that have additional desirable characteristics including tolerance of harsh, desiccated, long-term storage conditions and other characteristics as further described below. Selective pressure conditions comprising one or more stresses are used to create novel and stable strains that have such characteristics from parent strains of *P. fluorescens* that exhibit the desired BCA characteristics but lack the additional desired characteristics. Selective culture and pressure conditions may be used to create the novel strains having measured characteristics for long-term storage under desiccated conditions across a wide range of temperatures as well as other relative performance indices.

Three parent bacterial strains in particular (designated S11P12, P22Y05, and S22T04 herein) were found to have greatest commercial promise due to their ease of efficient, high yielding cultivation in liquid culture (a U.S. industry standard) while still retaining biocontrol efficacy. However, it should be appreciated that other parent strains may also be used in the methods of the invention to create novel strains having the desired identifying characteristics. This invention provides novel mutagenized strains having desired relative performance indices and methods of dry storage as well as resistance and tolerance to drying on a surface (e.g., a potato surface) after application. These novel bacterial antagonists lower costs and improve the convenience of application of the antagonist in the field and various storage conditions. To enhance the ability to manufacture a dry storage stable product to benefit the economics of biocontrol agent applications, the current invention relates to novel strains of Pseudomonads having enhanced tolerance for dry storage and maintaining desired capabilities of biological control of fungal potato storage diseases (e.g., dry rot, pink rot, late blight, etc.) and sprouting. The inventive dry storage tolerant strains of Pseudomonads were developed by being subjected to engineered mutagenesis from their respective parent strains through successive cycles of growth, followed by desiccation via drying (e.g., in micro-droplets to mimic low cost spray drying), and dry storage for increasing lengths of time. Initial viability loss may be prevented through the application of osmoprotectants to stabilize cell membranes and proteins (see e.g., Slininger, P. J. & Schisler, D. A. (2013) *Biocontrol Sci. Tech.* 23, 920-943; Schisler D. A., et al. (2016) *Biological Control.* 98:1-10); however, such application is more costly and it is desired in the present invention that osmoprotectants are not utilized. Higher quality osmoprotectants, such as trehalose and melezitose, are generally costly, and the more abundant, generally cheaper mono- and disaccharides (e.g., glucose, fructose, sucrose) may potentially support competing microbial populations that would detract from the desired bioefficacy of the disclosed novel strains. Other variables of the process train, such as conditions of cultivation, drying, storage, and rehydration may alternatively be analyzed and optimized using a high throughput screen.

For commercial use, an effective method of dry storage for these bacterial antagonists lowers costs and streamlines applications. To produce the novel strains of the invention, engineered mutagenesis is used in a strategic fashion to improve and/or enhance desiccation tolerance and other RPIs as compared to parent strains. The lack of such tolerance for parent strains of *P. fluorescens* requires an approach to reducing loss of cell viability during any event where the strains encounter a dry environment or are actively dried for storage purposes. Strain improvement via engineered mutagenesis is an approach that allows for enrichment of desired features in an organism by applying stress factors to force the population to become more concentrated in individuals that can adapt to thrive in the presence of those stress factors. In contrast to other molecular genetic methods (e.g., genetic engineering) that are useful to modify a few genes, the engineered mutagenesis methods of the present invention are a more effective approach to strain improvement when the anticipated changes needed are complex and are likely to involve a multitude of genes. For effective performance as a BCA rated based on RPI criteria, the novel strains must not only survive the drying process and long-term dry storage, but also revive and return to an active growing condition with retention of bioefficacy when challenged with disease-causing fungi in, for example, potato wounds.

In embodiments, the parent strain populations are subjected to a successive series of steps to achieve the improvement and/or enhancement in relative performance indices. An embodiment of the engineered mutagenesis process used to create the novel strains of the invention is illustrated as a flow diagram in FIG. 1. In step 1, a parent strain of interest is cultured using methods known in the art. For example, the culture is grown in a semi-defined liquid medium (SDCL) to a desired point of cell density. When the culture reaches a point of desired cell density (e.g., about $1\times10^9$ cells/mL or more preferably greater than about $1\times10^{10}$) and maturity (e.g., late growth to late stationary phase but before death phase) as determined by a skilled artisan (e.g., about 24 hours to about 96 hours culture time), a sample of the culture is removed and centrifuged to form a pellet of the cells of interest as shown in step 2. The pelletized sample of cells is then suspended in a suitable volume of culture medium depicted as step 3 and dispensed in prescribed amounts (e.g., about 10, about 50, or about 100 μL) into the wells of a dispensing plate (e.g., 96-well plate) shown as step 4. The samples are then aliquoted into, for example, 96-well plates for monitoring and transferring as shown in step 5. It should be appreciated that one with skill in the art could use any suitable culturing and dispensing techniques to split the initial culture into a desired number of subcultures/populations to subject to the subsequent stresses (e.g., various temperatures, dryness, and/or other conditions) as herein described for engineered mutagenesis and the creation of distinct mutagenized populations. Step 6, for example, depicts desiccation via rapid air drying of the plates having 1 μL droplets of the suspended cells in spent broth (without osmoprotectant). In embodiments, various methods of drying may be used, such as air drying, vacuum drying, spray drying, fluidized bed drying, and/or tray drying (each of the foregoing with or without the application of heat) and/or freeze drying. Any one or combinations of these drying methods may be used as selected by a skilled artisan. The mutagenized populations are then separately analyzed (e.g., on a plate reader to measure optical density) to assess whether any exhibit desired functions or properties with respect to desiccation tolerance in a superior or desired fashion over other mutagenized populations and the parent strain(s) as shown in steps 7 through 10. In step 7 through 9, an attempt is made to revive the dried populations in liquid culture, and in step 10 the optical density is measured to assess the state of each population. The populations are then sealed and stored for various storage periods and temperatures as shown in steps 12 through 14. Preferred temperatures are in the range of about −80° C. to about 37° C., or from about 0° C. to about 28° C., or about 25° C. Steps 7 through 10 are then repeated after the prescribed storage periods to assess the state of each population.

In embodiments, isolates of mutagenized populations might be ranked against parent strains as well as against other mutagenized populations using statistical relative performance indices (sometimes referred to herein as "RPI") for any number of factors. Such factor may include, for example, cell yield in mature aerobic cultures on SDCL medium or other suitable media; ability to suppress diseases, such as dry rot or other diseases caused by fungal pathogens including late blight (incited by *Phytophthora infestans*), pink rot (incited by *Phytophthora erythroseptica*), and *Pythium* leak (incited by *Pythium* spp.), etc.; sprouting during long-term storage of potatoes; level of active growth recovery within a time period after rehydration in a minimal medium (sometimes referred to herein as "MG" medium which is a type of medium that provides a dilute growth medium (e.g., dilute form of SDCL) intended to provide nutrients at low levels to revive and rehydrate dry stored cells). MG medium may contain nutrients of similar composition to other media as herein described but lower concentration than typically used for cell production. Desired resistance to dry storage times might be on the order of about one to two weeks, three weeks, several months, or over one or more years. Various temperatures may also be used to introduce an additional stress factor to the process. Examples of temperatures include both colder and warmer temperatures such as might be encountered in warehouses or farm buildings without climate control, where temperatures may range from subzero to extreme summer heat (e.g., about −20° C. to about 50° C. or any subrange therein).

In embodiments, the novel mutagenized strains are also tested for efficacy to continue suppression of agricultural maladies relative to the respective parent strains. For example, putative suppressive field soils could be mixed into soil sterilized via gamma irradiation so as not to change the quality of the soil but potentially via other methods such as UV or microwave irradiation, or autoclaving, or baking, or with chemicals, such as methyl bromide, etc. The *Fusarium*-inoculation might be added to the periderm-containing soil to allow enrichment of biological control agents able to compete with the pathogen and colonize the potato surface in various ratios (e.g., in about a 5:93:2 ratio—live soil: sterile soil:periderm). It should be appreciated that soil sterilization may have varying effects on soil composition and structure and should be considered by a skilled artisan performing this type of testing (see e.g., Darbar and Lakzian (2007) *Caspian J. Env. Sci.* Vol. 5 No. 2 pp. 87-91; Berns et al. (2008) *European Journal of Soil Science*, 59, 540-550). For enrichment of biological control agents from the live soil, the sterile soil would be the major amount and the live soil a minor amount. The periderm would also be a minor amount, as expected in the ambient potato field. Potato wounds remaining clear or substantially clear of disease after being pasted with the enriched soil mixture and incubated at typical healing temperatures (e.g., about 15° C., followed by longer term storage at about 3° C. (e.g., 2° C. to 4° C., or 3.3° C., or 3.5° C.) to about 7° C. (e.g., 6° C. to 8° C., or 7.2° C., or 7.5° C.) could be excavated and plated to isolate putative biocontrol strains. Temperatures may vary depending on the intended use of the product, such as for seed, process, or fresh pack. In a wounded potato bioassay screen, putative strains effective at preventing dry rot would be identified.

Mutagenized populations having superior relative performance indices may then be selected and subjected to additional stress conditions of varying intensities over an iterative series of steps (e.g., as illustrated in FIG. 1) as necessary to arrive at one or more mutagenized populations that has the desired functions and/or identifying characteristics. Other ranking systems might also be devised and applied, such as involving weighted parameters to prioritize ranking criteria based on economics or functional requirements in production or application. Examples of desirable characteristics as measured through relative performance indices of the mutagenized novel strains include retained growth and bioefficacy phenotypes that were at least about 1.6 times to as much as about 6 times, often about 2 to about 3 times, more active after rehydration from the dry condition than the corresponding parent strains. Species identity (e.g., based on 16s rRNA sequence analysis) is generally conserved from the parent strain to the novel mutagenized strain in preferred embodiments. Other methods known in the art may also be used to identify species, such as DNA-DNA hybridization, which is also a reliable though more laborious and costlier than 16s rRNA. The latter method is currently in greatest use for genus and species taxonomic identification. It was shown that the novel species invented through engineered mutagenesis and respective parent strains were the same species, indicating that uncontaminated cultures were maintained through the process of the invention.

The mutant strains are prepared for long-term desiccated storage using means generally available in the art. For example, aliquots of biocontrol agents can be dried using a variety of methods (as discussed herein) including, for example, air or vacuum drying with or without warming, freeze drying, spray drying, fluidized bed drying, and tray drying. Methods of drying that are low in cost to apply and allow high rates of cell survival are preferred, such as air drying in trays, spray, or fluidized bed drying. A room temperature air drying process at controlled humidity in trays is optimized for the BCAs of the invention with respect to formulation with osmoprotectant and carrier types. Depending on the carrier, osmoprotectants and extent of drying procedure used, the moisture content (in terms of wt. %) is usually less than about 4% but could be as high as about 30%. A preferred moisture level to prevent contaminant growth is less than 15% moisture. The formulation or composition for a commercial form of the novel mutant strains prepared for long-term storage may include other ingredients and stabilizers known in the art for bacterial formulations and storage. Examples of stabilizers that might be used include magnesium sulfate, potassium chloride, sodium chloride, potassium dihydrogen phosphate, Ringer's solution, Sabouraud broth, peptone, trehalose, sucrose, glucose, fructose, the like, and combinations thereof. For an additional listing of potential formulation additives see, for example, Bernhard, K., et al. (1998) Appendix I: A catalogue of formulation additives: Function, nomenclature, properties and suppliers. Pages 333-365 in: Formulation of Microbial Biopesticides: Beneficial Microorganisms, Nematodes and Seed Treatments. H. D. Burges, ed. Kluwer Academic Publishers, Dordrecht, the Netherlands).

It should be appreciated that particular formulations and compositions for various storage facilities may be optimized by one of skill in the art by evaluating a series of options through bioassays to select for desired tolerance levels as well as distribution and treatment methods for a target application. Desired tolerance levels (e.g., superiority of survival upon rehydration) may be achieved by varying the formulation depending upon the desired robustness of characteristics.

In embodiments, the invention also provides kits which are useful for carrying out methods of the present invention. The kit includes a container comprising compositions of the present invention and instructions for using the compositions for the purpose of controlling fungal populations as disclosed herein. The kits can comprise a first container means containing the compositions described herein. The kit can also comprise other container means having one or more solutions, diluents, or applicators necessary or convenient for carrying out the invention. The container means can be made of glass, plastic, foil, the like, and combinations thereof and can be any suitable vial, bottle, pouch, tube, bag, box, etc. The kit can also contain written information, such as procedures for carrying out the present invention or analytical information, such as the amount or concentration of the composition contained in the first container means. The container means can be in another container means (e.g., a box, bag, etc.) along with the written information. The amount of active ingredient (e.g., colony forming units of the novel strain(s)) in the compositions of the invention is/are present in an effective amount to deliver the prescribed dosages to the fungal populations based on, for example, an amount to be delivered to a target fungal population and/or an agricultural area such as a field or storage facility and/or a concentration range of the active ingredient. The composition may also be prepared from a more concentrated form such as a solid or powder dried and prepared as herein described and placed in a sachet or other container that would preserve its integrity until use which the user would mix with an aqueous diluent (or apply directly without dilution) to produce a composition to be applied to the desired area or agricultural product(s). The sachet could be opened and poured into the correct pre-measured amount of an aqueous diluent. Alternatively, the sachet type is selected from a variety of materials, such as biodegradable or bio-based plastic. Compatibility of particular ingredients in the kit would be determined for a given application by a skilled artisan. In a further embodiment, the liquid formulation could be encapsulated (e.g., hydrogels or other such material). The sachet or encapsulating material containing the composition may be an agriculturally acceptable carrier that dissolves and/or provides the composition in a time-released fashion.

In embodiments, novel BCA strains may also be produced and/or used as a broad spectrum antifungal microbial alternative to azole compounds on various sugar streams from, for example, hydrolyzed switchgrass which contains various compounds such as sugars, acetic acid, and furanaldehydes generated from lignocellulose. As such, broad spectrum antifungal microbial alternatives may be produced as a coproduct of a renewable lignocellulose in a biorefinery (e.g., bioethanol or biodiesel production) or in other bioconversion processes to leverage low cost renewable lignocellulosic biomass for the production and/or use of novel BCAs as biorefinery coproducts. In such embodiments, the strains would need to have tolerance against switchgrass hydrolyzates.

In embodiments, the invention may be used as part of an integrated pest management system and combined with chemicals and other BCAs. The BCAs of the invention may be applied in combination with other chemicals that are applied to potatoes postharvest for protection during storage. For example, the BCAs of the invention can be combined to varying degrees with SPROUT NIP (CIPC) potato sprout inhibitor (Loveland Products Inc.; Loveland, Colo.), STADIUM fungicide (a mixture of difenoconazole, azoxystrobin, and fludioxonil; Syngenta Participations AG; Basel, Switzerland), and PHOSTROL pesticide for agricultural use (phosphorous acid; Nufarm Americas Inc.; Alsip, Ill.) and may be advantageous in combination to reduce the application dosage of such chemicals needed for control. The BCAs of the invention may also be strategically combined with other treatments or used alone as applicable to achieve organic certifications.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Example: Engineered Mutagenesis

Materials and Methods

Parent Bacterial Strains and Cultivation. *Fusarium* dry rot suppressive strains *Pseudomonas fluorescens* S11:P:12 (NRRL B-21133), P22:Y:05 (NRRL B-21053), and S22:T:04 (NRRL B-21102) isolated previously (Schisler and Slininger, 1994) were stored lyophilized in the ARS Patent Culture Collection (NCAUR, USDA, Peoria, Ill.). Stock cultures of bacteria in 10% glycerol were stored at −80° C. Glycerol stocks were streaked to ⅕ strength trypticase soy broth agar plates (6 g/L Tryptic Soy Broth (Difco Laboratories, Detroit, Mich.); 15 g/L agar) which were incubated 2-3 days at 25° C. and refrigerated up to one week as a source of preculture inoculum. Pre-cultures containing 50 mL defined media (SDCL below) in 125-mL flasks were inoculated by loop and shaken at 250 rpm (2.5 cm eccentricity) and 25° C. Cells were harvested after 72 hrs and used to inoculate test cultures to an initial absorbance (620 nm) of 0.1 (~0.5-1×10$^8$ cells/mL). After 72 h incubation under conditions similar to pre-cultures, the test cultures were harvested. Two 5-mL samples were taken from each flask at 72-hrs for determining both $A_{620}$ and sugars by HPLC analyses. Then in centrifuge tubes at 4500 rpm the remaining cells were pelleted and concentrated to an $A_{620}=5$ in spent broth. The treatment cells were kept chilled on ice until the experiment was completed.

SDCL Medium for Flask/Fermentor Cultures. For cultivation of dry rot suppressive strains, semi-defined complete liquid (SDCL) medium (C:N 26:1) was prepared with 2 g/L each $K_2HPO_4$ and $KH_2PO_4$; minerals including 0.1 g/L $MgSO_4(7H_2O)$, 10 mg/L NaCl, 10 mg/L $FeSO_4(7H_2O)$, 4.4 mg/L $ZnSO_4(7H_2O)$, 11 mg/L $CaCl_2(2H_2O)$, 10 mg/L $MnCl_2(4H_2O)$, 2 mg/L $(NH_4)_6Mo_7O_{24}(4H_2O)$, 2.4 mg/L $H_3BO_3$, 50 mg/L EDTA; 0.01 g/L each of purine and pyrimidine growth factors adenine, cytosine, guanine, uracil, thymine; 0.5 mg/L each of vitamins thiamine, riboflavin, calcium pantothenate, niacin, pyridoxamine, thioctic acid; 0.05 mg/L each of vitamins folic acid, biotin, $B_{12}$; 15 g/L DIFCO Vitamin-free Casamino Acids, 0.15 g/L D,L-tryptophan, 0.6 g/L cysteine, and 15 g/L glucose (or carbon source as specified). Macro minerals, amino acids, glucose, and acidified purines and pyrimidines were autoclaved separately. Vitamins and trace minerals <0.1 g/L were filter sterilized. After combining sterilized ingredient groups, pH was adjusted to 6.8-7.0 with NaOH.

MG Medium for Microplate Cultures. Cells cultivated in 50 μL working volume microplate cultures were provided microplate growth (MG) medium. MG and SDCL media were the same except that the amino acids and glucose supplied to MG medium were reduced to one-fifth of the corresponding SDCL medium concentrations: 5 g/L DIFCO Vitamin-free Casamino Acids, 0.05 g/L D,L-tryptophan, 0.12 g/L cysteine, and 3 g/L glucose.

Engineered Mutagenesis Procedure. A small volume (10 mL) of the 72-h flask culture was centrifuged 4,500 rpm for 15 minutes in the Eppendorf 5804R (Eppendorf North America, Hauppauge, N.Y.), and cells were resuspended to an absorbance at 620 nm ($A_{620}$) of 5. A sample of each 72-h strain treatment was plated to determine initial viable cell count, then cells were kept chilled on ice until all plates (also on ice) were aseptically spotted with a 1 μL droplet of cell suspension in each well. Note that each microplate was loaded with a single bacterial strain to prevent cross-contamination of strains. Each of the three chilled bacterial strain suspensions was applied to duplicate 96-well microplates such that there was 1 μl delivered per each well of each of the duplicate 96-well plates. Once plates were spotted, they were removed from ice and allowed to dry 1 h in the biological hood. The dry plates were then rehydrated, grown for 24 h, and then transferred and dried in new sterile 96-well plates, grown again for 24 h, transferred 1 μL/well of six new replicate plates per each strain and dried again, and then dried plates were vacuum sealed at 100 mbar in sterile 3 mil, 6"×8" nylon/poly bags [catalogue #3R0608-100, Doug Care Equipment, Santa Clarita, Calif.] using a MULTIVAC vacuum packer (Multivac Sepp Haggenmüler SE & CO; Wolfertschwenden, Germany), and stored at 25° C. for three storage times (ranging initially from days to weeks and to eventually several months). Vacuum packing bags were sterilized by placing multiple bags in a 1,500-mL beaker covered with foil and heating a minimum of 72-hrs in a drying oven set at 50° C. For each bacterial strain line, three sets (A,B,C) of duplicate plates (total of six replicates) were always prepared in this way and stored for assessment of cell survival at three different storage times. For each strain, one pair of duplicates was assessed at each storage time—a monitoring plate for plate reading and a transfer plate for preparing a new set of six replicate plates to prepare for another dry storage period. Only the bacterial population from the one pair of plates (A, B, or C) retaining active cells for the longest of the three storage times was carried forward in the engineered mutagenesis process. Since each pair of plates in the six-plate set was evaluated at a different time point, six newly spotted micro-plates and duplicate 20% glycerol stock cultures for −80° C. storage in cryovials were prepared for each evaluation point. The glycerol stocks were prepared from the transfer plates by mixing pooled wells 1:1 with sterile 40% glycerol. However, only the glycerol stocks and plate set prepared from the longest stored plates with active surviving populations were retained in the engineered mutagenesis process cycle, while the others from the lesser storage times were discarded.

At the conclusion of a storage period, microplates were assessed for viable cell survival, and cultures were prepared for another round of enrichment for desiccation tolerant cells. Prior to opening the vacuum sealed plates, they were placed in the biohazard hood. The vacuum sealed plates were cut open with ethanol sterilized scissors or a sterile scalpel. The cells in the two stored micro-plates for each strain were resuspended by adding 50 μL MG medium to each well. One plate, the transfer plate, was to remain unopened during the growth period. It was used to make the cell transfer to two new plates after the 24-h growth period. The second plate was used to monitor growth. The plates were shaken for 15 minutes initially using a moderate plate shaker setting allowing good mixing without splashing. Cell growth was then monitored initially and later at 24 h, and at 48 h if no significant growth at 24 hr, using a Power Wave XS plate reader to assess the monitoring plate only. Between readings, both micro-plates were incubated at 25° C. in autoclaved plastic boxes with sterile WYPALLS disposable wipes towels (Kimberly-Clark, Dallas, Tex.) soaked with 40 mL sterile deionized $H_2O$. Prior to reading, the plates were shaken 15 sec at a moderate shaker setting to resuspend cells without splashing.

As storage times lengthened and growth recovery in wells became sparse, a modified desiccation tolerance enrichment cycle was carried out prior to long term storage. After growth reached >0.10 absorbance units, as read by the plate reader with 96-well plates filled to 50 μL, 1-μL volumes were spotted from each well of the unopened transfer plate to the appropriate well of two new 96-well plates to make a new transfer plate and a new monitoring plate. If growth did not occur in all of the plate wells, cells from the wells that did grow were pooled and used to spot new storage plates. The plates were allowed to dry in the hood for 1-h and then the cells were resuspended again in 50-µL MG medium/well and again monitored after 24-h growth. The 1-µL spotting, drying, rehydrating, and growth cycle was repeated as appropriate to improve the percentage of wells with growth recovery. Following recovery of growth in over 50% of wells in a 24-h incubation period to enrich drying tolerant cells, culture from pooled wells was spotted to microplates for a short term 24- to 72-h storage period to further enrich drying tolerant cells able to survive a short storage. When plates were ready to be prepared for long term storage, 6 replicate plates (A, B, C duplicate plate sets) per each strain were spotted, dried, and then vacuum sealed for storage at 25° C. for weeks extending to months. The choice of storage times included the current longest storage time (6 weeks, for example) and two longer times, advancing the storage time generally by two weeks (7 weeks and 8 weeks, for example).

Monitoring Species Characteristic Phenotype Retention with Indicator Plates. As strain mutagenesis progressed, populations were plated onto indicator media to ensure that certain features of metabolism advantageous to competitiveness as biological control strains were retained. The following King's Medium B (KMB) was used to check the maintenance of colony fluorescence due to siderophore production by all three strain lines: 20 g/L Proteose Peptone #3 (DIFCO_Laboratories, Detroit, Mich.); 10 g/L glycerol, 1.5 g/L $K_2HPO_4$, 1.5 g/L $MgSO_4(7H_2O)$, and 15 g/L Agar. Siderophores aid in iron scavenging for survival and fluorescence can be easily visualized in an ultraviolet light box. Additionally, strain P22Y05 is uniquely able to grow competitively given only histidine as sole carbon source. And the following minimal defined liquid medium (MDL) combined with tetrazolium red and agar was used to track retention of this ability in plated populations: 2 g/L $K_2HPO_4$, 2 g/L $KH_2PO_4$ 0.01 g/L $FeSO_4(7H_2O)$, 0.1 g/L $MgSO_4(7H_2O)$, 0.01 g/L NaCl, 0.0044 g/L $ZnSO_4(7H_2O)$, 0.011 g/L $CaCl_2(2H_2O)$, 0.01 g/L $MnCl_{2.4}H_2O$; 0.002 g/L $(NH_4)_6Mo_7O_{24}(4H_2O)$, 0.024 g/L $H_3BO_3$, 0.05 g/L EDTA, 1.26 g/L urea, 5 g/L histidine, 0.05 g/L 2,3,5-triphenyl-tetrazolium chloride, 15 g/L agar. For strain P22Y05, colonies at 24-48 h were white and ~1 mm in diameter. At 48-72 hrs these colonies have become dark red and >1 mm in size with slight, clear borders. Other *Pseudomonas fluorescens* strains do not grow well on MDL medium and are not any larger than a ~0.2 mm in diameter and remain white. This medium can allow counting of the 48-72 h colonies of P22Y05 in mixed cultures, and was originally developed to monitor its relative population level in co-cultures with S22T04 and S11P12, which have been shown to improve biological control efficacy and consistency (see e.g., Slininger, P. J., et al. (2010) *Biocontr. Sci. Technol.* 20(8):763-786). Additionally 1/5 TSA prepared with 0.05 g/L 2,3,5-triphenyl-tetrazolium chloride was also useful in visualizing the retention of marginalan production by strain S11P12 which appears as a slimy colony with red concentric rings. In previous studies, marginalan production was shown to be beneficial to desiccation survival of S11P12 (see e.g., Slininger, P. J., et al. (2010) *Biocontrol Sci. Technol.* 20(3):227-244). Additionally, plating on ⅕ TSA with tetrazolium red accentuates differences in colony morphologies to aid in visualization of culture changes and to perhaps signal entry of a contaminant.

Isolation of Tolerant Single Cells from Evolved Cultures Following Long Term Dry Storage. Selected six-microplate storage sets prepared as explained above were retrieved from dry storage and rehydrated with 50 µL/well of MG medium and then shaken 15 min on a microplate shaker set at a medium speed to prevent splashing. The rehydrated plates were placed in an autoclaved hinged 1000-µL pipette tip box containing an autoclaved WYPALL disposable wipes (Kimberly-Clark, Dallas, Tex.) on the bottom, moistened with 40-mL sterile deionized $H_2O$. The plates were incubated at 25° C. for 24-48 h until growth was first seen in some of the wells of plates with the same date. After growth was observed in all or some of the wells of identically-dated plates, ~6 wells (potentially one strong well from each plate of the six plates) were pooled and then microdilution plated onto 1/5 TSA. Serial dilutions were carried out at the 1 mL scale in 24-well plates using phosphate buffer as diluent [Phosphate Buffer (Wastewater) Mf #LM008-PB99, Fisher #NC9718063]. The 1/5 TSA plates were incubated at 25° C. for 24-48 h until growth was seen. As soon as growth was seen on the 1/5 TSA plates, ~5 representative colonies were picked from each storage plate set spotted on the same date. Each picked colony was purity streaked onto a 1/5 TSA plates for glycerol stock preparation. After 24-h the cells were harvested by flooding the plate with 6-mLs sterile 20% glycerol, gently scraping the surface of the plate with a sterile loop, and dispensing 1.5 to 2.0-mL aliquots to 2 or 3 sterile cryovials. The prepared stocks were stored frozen at −80° C. then streaked onto indicator plates along with the wild type parent strain to check colony morphology phenotypes.

Mutagenized Species Confirmation by 16S rRNA Sequencing. The 16S rRNA gene provides a species specific signature sequence which is useful for bacterial identification process. To confirm that the species of final mutagenized strains matched the parent species 16S PCR and seqeuncing was done. To prepare for DNA extraction, glycerol stock cultures of parent strains and isolates of mutagenized cultures were purity streaked and incubated 24-hrs at 25° C. 10-mL cultures in 50-mL flasks of SDCL were incubated 24-hrs at 25° C., 300 rpm (1" stroke). Genomic DNA extraction from each culture was carried out using a MASTERPURE Gram Positive DNA Purification Kit (Epicenter, Madison, Wis.) following the manufacturer's instructions. Briefly, for each isolate, 1 mL of culture was centrifuged in a microfuge tube (Fisher Scientific, Hampton, N.H.) at maximum rpm setting in a refrigerated bench top centrifuge (13,200 rpm) for 4-minutes. Using a 1-mL pipettor with pre-sterilized filtered pipette tips, supernatant was removed from each pellet, changing tips between tubes. Cell pellets were refrigerated and then used for the DNA extraction. To each pellet was added 150 µl of TE buffer and 1 µl of READY-LYSE lysozyme solution (Lucigen Corporation; Middleton, Wis.), changing tips between each microfuge tube. Tubes were clipped into a multi-tube shaker (such as, MULTI REAX shaker from Heidolph; Schwabach, Germany) and vortexed at maximum speed for 5 to 10 min pending the tightness of the pellets. Then tubes were incubated at 37° C. for a minimum of 30 minutes per strain based instructions of the kit. 150 µl of the Proteinase K/Gram Positive Lysis Solution was then added to each sample followed by 1 µl of Proteinase K (50 mg/ml) to each 1-mL culture pellet in microfuge tubes, placing the pipet tip into liquid to dispense, changing tips between each microfuge tube, and finally vortexing all tubes. Tubes were incubated at 65-70° C. for 15 minutes, vortexing briefly half-way through the incubation period and again at the end. Samples were cooled 5-minutes in a 37° C. heating block and then further by placing on ice for 3-5 minutes, or in a freezer −20° C. for 5 minutes, or at −80° C. for ~2 minutes.

DNA precipitation was initiated by adding 175 µL of chilled MPC Protein Precipitation Reagent (Lucigen Corporation; Middleton, Wis.) to each 300 µL of lysed sample, then vortexing thoroughly for ~10 seconds/sample. The debris was pelleted by centrifugation at 4° C. for 10 minutes in a refrigerated microcentrifuge (~13200 rpm for >10,000× g). Using a 1-mL pipette, the supernatant (500-600 µL) was transferred to a clean microfuge tube, and the pelleted debris was discarded, using a clean pipette tip for each sample. Mixing thoroughly, 1 µL of RNase A (5 µg/µL) was added to each sample. Samples were incubated at 37° C. for 30-minutes (<2 h) in a heating block. After adding 500 µL of isopropanol to the recovered supernatants, tubes were simultaneously inverted 30-40 times in a tube rack. DNA was pelleted at 4° C. for 10 minutes at >10,000×g in a microcentrifuge. Supernatants were pipetted off with a clean tip to remove remaining isopropanol without dislodging the DNA pellet. To rinse, 50 µl of 70% ethanol was delivered to the side of the pellet, then removed, leaving the pellet (repeating centrifuging as needed). For 16S rRNA analysis the DNA was suspended in 55 µL of TE Buffer, or for Ion Torrent analysis, it was suspended in water. Samples were frozen at −20° C. for subsequent DNA analysis.

PCR sequencing was performed with primers 27F and 1492R indicated as SEQ ID NO: 1 and SEQ ID NO: 2, respectively, using AMPLITAQ GOLD enzyme reagents for scientific use (Roche Molecular Systems; Pleasanton, Calif.) PCR master mix under the following conditions: initial denaturation 95° C. for ten minutes; followed by 35 cycles of 95° C. for 30 seconds, 55° C. for 30 seconds, and 72° C. for one minute; and a final extension at 72° C. for seven minutes. Amplification products were purified using MONTAGE PCR Cleanup Filter Plates (Millipore, Billerica, Mass.). Sequencing reactions were conducted using the ABI BIGDYE version 3.0 sequencing kit (Applied Biosystems, Foster City, Calif.) following the manufacturer's suggested protocol, but at one-tenth the recommended volume. Reaction products were purified using the BIGDYE XTERMINATOR DNA purification kit (Applied Biosystems, Foster City, Calif.) following the manufacturer's suggested protocol and sequenced on an ABI3730 genetic analyzer (Applied Biosystems, Foster City, Calif.) using the aforementioned oligonucleotide primers. Resulting DNA sequences were visually edited and assembled using SEQUENCHER 5.4 DNA sequencing software (Gene Codes Corporation, Ann Arbor, Mich.). Consensus sequences were aligned and compared using CLC_Bio genomics workbench 10.0 software (Qiagen Inc., Germantown, Md.).

Wounded Potato Bioassay of Dry Rot Disease Suppressiveness of Mutagenized Strains. Putative mutagenized bacterial isolates to be evaluated were precultured for 24 h then transferred to similar 50-mL flasks containing 10 mL SDCL medium with 10 g/L glucose and closed with silicon sponge plugs. The growth cultures were inoculated to $A_{620}$ 0.1 and were shaken at 25° C., 300 rpm (1" stroke) for 72 h. At harvest the growth cultures were assessed with respect to final $A_{620}$, viable cells/mL, pH and residual glucose. Bacterial isolate treatments were diluted by mixing 72-h cultures with chilled buffer to obtain $A_{620}$ of 0.15-0.17, and then 1:1 (v/v) with *Gibberella pulicaris* (Fr.:Fr.) Sacc. (anamorph: *Fusarium sambucinum* Fuckel) R-6380 to deliver either 1 or 3×10⁶ conidia/mL (by hemacytometer count). Treatments were kept on ice while potatoes were treated. Potato wounds made with a 2 mm diameter×2 mm length steel pin were thus co-inoculated with treatment and pathogen by pipetting 5 µL of the 1:1 (v/v) treatment:pathogen mixture to each wound. Each bacteria treatment was repeated on one wound per each of six different size B Russet Burbank seed potatoes free of sprout inhibitor or chemical fungicides (Wisconsin Seed Potato Certification Program, University of Wisconsin Madison, Antigo, Wis.) that had been washed and dried a day ahead at room temperature, following prior storage in a cold room ~4° C. Each potato had four wounds equally spaced around the middle with three wounds receiving bacteria and pathogen and one control wound receiving only pathogen mixed with buffer. Three extra potatoes were inoculated with the control treatment in each of the four wounds per potato. Each potato was placed in a plastic weigh boat on a dry 2.54 cm-cut square of WYPALL L40 all-purpose disposable wipe. Boats were held in trays that were supplied two dry WYPALL disposable wipes over the top of potatoes and two WYPALL disposable wipes wet with 40 mL of water each and placed on either side of the tray, plastic bagged, and stored 21 days at >90% relative humidity and 15° C. After storage each potato was quartered, slicing through the center of each of the four wounds. The extent of disease in each wound was rated by adding the greatest depth and width measurements (mm) of discolored necrotic tissue extending below and to the sides of the wound. Relative disease (%) was calculated as 100× (wound disease rating/average disease rating of wounds receiving pathogen only).

Microplate Droplet Drying Assay of Desiccation and Storage Survival of Bacteria. Putative mutagenized bacterial isolates were grown 72 h and growth parameters were assessed as described above in the procedure for the wounded potato bioassay of dry rot suppressiveness. Upon harvest, enough of each culture was centrifuged (7,000 rpm) to obtain $A_{620}$=15 when reconstituted to 500 µL in supernatant spent broth. All treatments were maintained chilled on ice during preparation and spotting to microplates that were also maintained on ice to prevent spot evaporation while all microplates were being spotted. A column of 8 wells per microplate was spotted with 1 µL of a treatment per each well. Each treatment was additionally spotted to 8 wells of a second replicate plate. Ten treatments were spotted simultaneously with initial and final water wells to prevent evaporation bias. This was accomplished by using a separate microplate for dispensing, which was loaded with 100 µL water in the first well, 10 treatments at 100 µL per well in the next 10 wells, and then 100 µL water in the twelfth. A twelve-channel pipette was then used to pick up treatments from the dispensing plate to deliver to the treatment plate, repetitively filling all 8 rows down the plate with water in the first well, the 10 treatments in the next 10 wells, and water again in the last of the 12 wells. A set of duplicate plates was prepared for each storage time (e.g., 0 h, 7 d, 14 d, 21 d, 28 d, or as appropriate per results). For each group of 10 treatments to be tested for dry storage survival, 10 micro-plates were spotted (i.e., 2 duplicate plates×5 storage times). For 20 treatments, 20 micro-plates would be spotted, and so forth.

As a control, the plates for the 0-hr storage time represent the case in which cell droplets were not dried, and these plates were prefilled with 50 µL MG per/well before spotting with treatments. Once spotted, the plates to be dried, which were not prefilled, were removed from ice, and placed in the biological cabinet to dry 1 hour with lids open. The plates prefilled with 50 µL MG medium/well were read on the BIOTEK POWERWAVE XS plate reader (Bio Tek Instruments; Winooski, Vt.) immediately after spotting and then again at 5, 8, 24, 30, and 48 hours to monitor recovery of growth. After 1-hr drying, the remaining plates were vacuum sealed and stored at 25° C. for storage (as described above for the dry storage of the engineered mutagenesis process). Plates were retrieved from storage at designated times, opened in the biological hood as described above and treatment wells in columns 2-11 were filled with 50 µL MG medium per well. Columns 1 and 12 wells were filled with 50 µL water to prevent evaporation bias of the treatments. During the growth assay, plates were incubated statically at 25° C. in plastic boxes with moist WYPALL disposable wipes to maintain humidity to further minimize evaporation.

Ranking of Mutagenized Strains. Mutagenized strains were ranked relative to their respective parent strain using three parameters: viable cell yield (Y) during growth, efficacy (E) in suppression of dry rot disease, and cell growth recovery after dry (D) storage. Statistical relative performance indices (RPI) were calculated to rank strains based on each factor: $RPI_Y$, $RPI_E$, and $RPI_D$. RPI is a dimensionless value that is useful in combining data sets to use in overall ranking or statistical analysis of treatments submitted to various testing procedures. Given disease or sprout ratings normally distributed across the group of bacteria stains tested, the value of $F=(X-X_{avg})/s$ ranged from −2 to +2. Here, X designated a cell yield, cell regrowth after dry storage, and dry rot disease rating observed for each isolate. $X_{avg}$ and s are the average and standard deviation, respectively, of all values observed for the group of bacteria treatments for a given parameter. Since F increases with increasing viable cell yield or cell growth recovery rate, then $RPI=(F-2)\times 100/4$, such that the value of RPI ranges from ~0 to 100 percentile from least to most yield or growth rate. However, since F decreased as disease suppressiveness improved, then $RPI=(2-F)\times 100/4$, such that the value of RPI ranged from ~0 to 100 percentile from least to most suppressive, respectively.

Absorbance Measurements of Culture Biomass. Cell biomass productions in flask cultures was assessed based on measurement in cuvettes with 1 cm path length using a GENESYS 5 spectrophotometer (Thermo Electron Scientific Instruments; Madison, Wis.). For 96-well microplate growth cultures, readings were taken on the BIOTEK Power Wave XS plate reader where pathlength of wells was set by the depth of the 50 µL medium used to fill wells for growth studies. Plates were read with lids on to maintain pure cultures.

Residual Glucose Measurements. High performance liquid chromatography (HPLC) was applied to assay glucose concentrations in cultures.

Statistical Analysis. Analysis of variance (ANOVA) was performed using SIGMASTAT statistical software (SPSS, Inc.) to determine significant main effects and interactions of the variables tested. Pair-wise comparisons were made using Student Newman Keuls (SNK) post hoc test for differences in means. The significance criterion applied was generally $P \leq 0.05$.

Results and Discussion

Strains, which were improved in desiccation tolerance, were evolved from their respective parents in microplates by subjecting populations to successive cycles of the steps shown in the FIG. 1 flow diagram of the engineered mutagenesis process: (a) growth in a low cost liquid medium (SDCL to start or MG in subsequent cycles); (b) desiccation via rapid air drying in 1 µL droplets of spent broth (without added osmoprotectant); (c) dry storage for increasing time in vacuum-sealed bags at 25° C.; and (d) rehydration in minimal medium (MG).

Tables 2 to 4 summarize the resulting variation of evaluation factors among putative mutagenized strains and the respective parent strain of three performance qualities used in ranking the mutagentized BCA isolates relative to parent strains: 72-h viable cell yield on a low-cost growth medium (SDCL) shown in the first column; 24-h growth recovery ($A_{620}$) upon rehydration in 50 µL MG medium after dry storage 21 d shown in the second column; and dry rot disease suppressiveness of cells grown 72-h on SDCL shown in the third column. Compared with parent strains, the highest ranked mutagenized isolates retained growth and bioefficacy phenotypes but were significantly more active after rehydration from the dry condition than the corresponding parent strains P22Y05 and S11P12, respectively. While growth recovery after rehydration of dry tolerant variants of S22T04 was similar to that of dry tolerant S11P12 isolates, active growth of the S22T04 parent strain was not recovered within the 24-h monitoring time interval.

TABLE 2

| Parent Strain S22T04 | | | |
|---|---|---|---|
| Isolate | Culture Cell Yield × $10^{10}$ (cfu/mL)[a] | Droplet Regrowth $A_{620}$ (30 h)[a] | Relative Disease (%)[a] |
| T04-135d-1 | 0.046 ± 0.053 a | 0.057 ± 0.005 e | 26.0 ± 22.6 a |
| T04-135d-2 | 0.199 ± 0.147 a | 0.072 ± 0.040 de | 33.2 ± 23.6 a |
| T04-135d-3 | 0.053 ± 0.000 a | 0.270 ± 0.040 a | 25.7 ± 20.9 a |
| T04-135d-4 | 0.095 ± 0.080 a | 0.060 ± 0.002 e | 30.0 ± 26.1 a |
| T04-135d-5 | 0.059 ± 0.032 a | 0.058 ± 0.002 e | 47.2 ± 44.1 a |
| T04-135d-6 | 0.032 ± 0.024 a | 0.051 ± 0.002 e | 22.7 ± 19.6 a |
| T04-135d-7 | 0.072 ± 0.021 a | 0.060 ± 0.003 e | 30.5 ± 30.3 a |
| T04-135d-8 | 0.076 ± 0.006 a | 0.063 ± 0.013 de | 47.9 ± 31.4 a |
| T04-135d-9 | 0.103 ± 0.018 a | 0.059 ± 0.011 e | 22.8 ± 14.2 a |
| T04-135d-10 | 0.102 ± 0.025 a | 0.056 ± 0.005 e | 40.1 ± 38.3 a |
| T04-42d-A11 | 0.053 ± 0.072 a | 0.063 ± 0.050 de | 48.6 ± 39.3 a |
| T04-42d-A12 | 2.110 ± 0.488 b | 0.111 ± 0.097 e | 12.8 ± 6.0 a |
| T04-42d-B1 | 0.049 ± 0.038 a | 0.049 ± 0.001 e | 21.7 ± 11.0 a |
| T04-42d-B2 | 0.094 ± 0.044 a | 0.058 ± 0.002 e | 38.0 ± 27.8 a |
| T04-42d-B7 | 0.079 ± 0.058 a | 0.067 ± 0.031 de | 42.2 ± 46.4 a |
| T04-42d-B12 | 0.054 ± 0.037 a | 0.057 ± 0.002 e | 39.0 ± 30.5 a |
| T04-42d-C3 | 0.727 ± 0.952 a | 0.066 ± 0.021 de | 43.4 ± 38.2 a |
| T04-42d-F12 | 0.035 ± 0.020 a | 0.069 ± 0.036 de | 26.9 ± 17.9 a |
| T04-126d-F4 | 1.400 ± 0.846 a, b | 0.150 ± 0.104 b | 10.0 ± 2.1 a |

TABLE 2-continued Parent Strain S22T04

| Isolate | Culture Cell Yield × $10^{10}$ (cfu/mL)[a] | Droplet Regrowth $A_{620}$ (30 h)[a] | Relative Disease (%)[a] |
|---|---|---|---|
| T04-126d-F10 | 1.250 ± 0.704 a, b | 0.108 ± 0.103 cd | 15.1 ± 11.0 a |
| T04-WT | 1.080 ± 0.709 a, b | 0.047 ± 0.001 e | 13.8 ± 18.4 a |

[a]Values designated with at least one letter in common are not significantly different at the P < 0.05 level.

TABLE 3

Parent Strain P22Y05

| Isolate | Culture Cell Yield × $10^{10}$ (cfu/mL)[a] | Droplet Regrowth $A_{620}$ (24 h)[a] | Relative Disease (%)[a] |
|---|---|---|---|
| Y05-179d-1 | 3.88 ± 3.71 a | 0.327 ± 0.065 a | 21.3 ± 15.7 a |
| Y05-179d-2 | 1.20 ± 0.42 a | 0.363 ± 0.039 a | 57.8 ± 72.7 a |
| Y05-179d-3 | 1.33 ± 0.25 a | 0.358 ± 0.055 a | 34.9 ± 42.9 a |
| Y05-179d-4 | 1.35 ± 0.10 a | 0.340 ± 0.057 a | 44.9 ± 49.7 a |
| Y05-179d-5 | 0.54 ± 0.23 a | 0.351 ± 0.050 a | 30.7 ± 36.9 a |
| Y05-214d-1 | 0.74 ± 0.16 a | 0.340 ± 0.057 a | 44.6 ± 95.5 a |
| Y05-214d-2 | 0.67 ± 0.22 a | 0.336 ± 0.059 a | 25.5 ± 38.6 a |
| Y05-214d-3 | 0.69 ± 0.09 a | 0.360 ± 0.041 a | 46.6 ± 92.5 a |
| Y05-214d-4 | 1.60 ± 0.78 a | 0.371 ± 0.029 a | 35.8 ± 61.0 a |
| Y05-214d-5 | 0.52 ± 0.10 a | 0.370 ± 0.030 a | 18.3 ± 24.0 a |
| Y05-228d-1 | 0.96 ± 0.23 a | 0.390 ± 0.011 a | 21.7 ± 40.7 a |
| Y05-228d-2 | 0.80 ± 0.21 a | 0.365 ± 0.030 a | 23.6 ± 26.0 a |
| Y05-228d-3 | 1.08 ± 0.46 a | 0.374 ± 0.036 a | 31.5 ± 41.4 a |
| Y05-228d-4 | 0.66 ± 0.01 a | 0.376 ± 0.041 a | 38.0 ± 44.4 a |
| Y05-228d-5 | 0.44 ± 0.18 a | 0.379 ± 0.021 a | 36.1 ± 39.6 a |
| Y05-241d-1 | 0.57 ± 0.00 a | 0.385 ± 0.024 a | 50.9 ± 67.1 a |
| Y05-241d-2 | 1.42 ± 0.57 a | 0.371 ± 0.043 a | 46.6 ± 52.0 a |
| Y05-241d-3 | 1.88 ± 1.24 a | 0.380 ± 0.035 a | 62.8 ± 70.8 a |
| Y05-241d-4 | 1.65 ± 0.64 a | 0.379 ± 0.029 a | 67.9 ± 106.3 a |
| Y05-241d-5 | 2.14 ± 0.08 a | 0.282 ± 0.045 b | 49.3 ± 47.0 a |
| Y05-WT | 2.00 ± 0.03 a | 0.209 ± 0.162 c | 75.5 ± 92.7 a |

[a]Values designated with at least one letter in common are not significantly different at the P < 0.05 level.

TABLE 4

Parent Strain S11P12

| Isolate | Culture Cell Yield × $10^{10}$ (cfu/mL)[b] | Droplet Regrowth A620 (24 hr)[b] | Relative Disease (%)[b] |
|---|---|---|---|
| P12-42d-A1 | 0.733 ± 0.166 a | 0.324 ± 0.006 a | 53.3 ± 50.4 bc |
| P12-42d-B1 | 0.482 ± 0.132 a | 0.060 ± 0.002 b | 65.1 ± 41.9 c |
| P12-42d-D5[a] | 0.653 ± 0.372 a | 0.084 ± 0.028 b | 47.1 ± 38.6 bc |
| P12-42d-D9[a] | 0.701 ± 0.410 a | 0.306 ± 0.055 a | 21.4 ± 27.1 ab |
| P12-42d-D10[a] | 0.643 ± 0.368 a | 0.264 ± 0.078 a | 8.4 ± 8.1 a |
| P12-WT[a] | 0.796 ± 0.350 a | 0.109 ± 0.056 b | 12.6 ± 10.4 ab |

[a]These Isolates had an extra set of replication
[b]Values designated with at least one letter in common are not significantly different at the P < 0.05 level.

The strain isolate names indicate the number of days in storage for the stored microplate plate from which they were isolated. Typically, each cycle through the engineered mutagenesis scheme gained two more weeks of successful storage survival for each of the three strain lines, and each cycle of the engineered mutagenesis scheme added about 10 cell generations. The approximate generation times associated with isolate types showed that significant phenotype changes could be observed after ~30 generations (i.e., cell doubling during propagation) of cell growth in the case of the S11P12 strain line. However, highest ranking isolates in longer engineered mutagenesis experiments, as for S22T04 and P22Y05, were obtained after a total sequence of ~180 generations.

Twenty putative desiccation tolerant isolates of strain S22T04 were summarized in Table 2 with respect to three key performance qualities used to evaluate and rank strains. Although 19 of 20 showed improvement over the wild-type parent strain, only 4 were capable of significantly faster regrowth from dried droplets of cell suspension based on plates read at 24-h after a 21-d storage. Considering cell yield from growth cultures and dry rot disease suppression, these strains outranked the parent strain and all other strains. This rank is particularly evident in the stacked bar graph of the RPI values based on each of the three performance factors for each isolate as shown in FIG. 2. The four top desiccation-tolerant isolates having total RPI>230 compared with about 195 for the parent S22T04 were: T04-135d-3, T04-42d-A12, T04-126d-F4, and T04-126d-F10. Strain T04-42d-A12 was the highest ranked strain with RPI 275, outranking the parent strain for each of the three parameters. It is notable that strain T04-135d-3 showed the most rapid regrowth, reaching 0.27 $A_{620}$ in 24 h, but on average it did not control disease as well and did not yield as many cells in growth culture as many of the other strains. All isolates formed fluorescent colonies when grown on KMB agar and matched the taxonomic identity of the parent strain by 16S rRNA gene sequence confirmation. The 16S identity of the strain S22T04 line was closest to *Pseudomonas rhodesiae*, but it is a novel species.

All twenty of the isolates plated from the engineered mutagenesis of P22Y05 were significantly improved in desiccation tolerance and showed more rapid recovery of growth within 24 h after rehydration in 21-d stored plates (Table 3). All of the mutagenized isolates also protected potatoes better than the parent strain, although most showed a decrease in viable cell yield when grown on SDCL medium. Considering overall ranking reflected in the total of relative performance indices based on the three evaluation factors (cell yield, dried droplet regrowth, and dry disease suppression) as shown in FIG. 3, eight strains outranked the wild-type parent strain performance and had RPI>160: Y05-179d-1, Y05-179d-3, Y05-214d-4, Y05-214d-5, Y05-228d-1, Y05-228d-2, Y05-228d-3, Y05-241d-2. Strain Y05-179d-1 was ranked the highest of all the isolates having RPI of 245 when RPI values of each type were summed. It demonstrated a very high cell yield on SDCL medium and showed the highest level of dry rot disease suppression in potatoes. Its ability to regrow from 21-d plates was significantly better than the wild type but a little less than many of the other isolates, though not significantly less (P>0.05). All isolates grew as fluorescent colonies on KMB agar and were distinguishable from the other two species S22T04 and S11P12 since they retained the ability to form deep red colonies when grown on MDL medium with histidine (data not shown). All isolates matched the species identities of the parent strain *Pseudomonas simiae* based on the 16S rRNA gene sequence.

Five putative desiccation tolerant isolates and the parent strain S11P12 were found to all match the 16S rRNA sequence identity of *Pseudomonas koreensis*. Additionally, colonies of the isolates were fluorescent on KMB medium and retained the feature of forming large slimy colonies with red target concentric circles when plated onto 1/5 TSA with tetrazolium red (data not shown). Three of the five isolates were able to grow significantly more rapidly than the parent strain from dried droplets of cell suspension, reaching as high as $A_{620}$ of 0.324 within 24 h after rehydration of the 21d stored microplate (see Table 4). The three top strains included: P12-42d-A1, P12-42d-D9, and P12-42d-D10. Average relative disease allowed by strain P12-42d-A1 was relatively high, 53.3% (Table 4), which was significantly higher than that allowed by P12-42d-D10, but not significantly higher than the others. All strains had similar production culture cell yields. Strain P12-42d-D9 was ranked highest overall with an RPI total of 190 for all three evaluation factors combined (FIG. 4).

Relationship of Selection Pressure Design to Strain Improvements Beneficial to Manufacturing Economics. Although the main purpose of the engineered mutagenesis scheme was to enrich for cells with improved drying and storage tolerance, the process also enriched, or at least maintained, other qualities beneficial to manufacturing economics. In the original ranking of the parent strains for commercial application, they ranked highly because they could both grow rapidly in liquid media of varying nutritional richness and could suppress *Fusarium* dry rot disease after being harvested from liquid culture (see e.g., Slininger et al. 1994). The engineered mutagenesis protocol was designed to maintain the industrially preferred liquid cultivation trait by incorporating growth on a prototype low cost liquid medium (see e.g., Zabriski, et al., (1980) Fermentation Media Formulation. In: Trader's Guide to Fermentation Media Formulation. *Memphis, Tenn.: Trader's Protein*. pp. 1-39) as a link in its cyclic chain of processes. The mutagenesis protocol would enrich for cells able to grow rapidly for harvest after a short cultivation (24 h) on a low-cost growth medium (MG), which are desired features of cost-saving manufacturing. The MG medium was designed to be similar to SDCL medium with amino acid and glucose strengths reduced to ⅕ in order to support abundant cell growth with little residual sugar as potential osmoprotectant during spotting to start the next drying and storage cycle.

Since cells were dried in spent culture medium without addition of osmoprotectants, the artificially created stress conditions would favor cells able to survive drying and storage without provision for cell separation or washing steps and without osmoprotectants, all cost-saving advantages. In a prior survey of process conditions optimizing cell desiccation and storage survival, the presence of spent culture broth during drying, especially in the absence of added osmoprotectants, was generally determined to be significantly detrimental for the survival of six of seven *Pseudomonas* strains included in that study. Only strain S11P12, which makes marginalan as a protective polysaccharide appeared to benefit from the presence of spent culture medium. This further suggests the general utility of incorporating spent broth into the cell drying step of the engineered mutagenesis as a means to select for drying protective phenotypes.

Due to their low resiliency to desiccation, the more successful processes generally applied for maintaining *Pseudomonas* spp. strains in long-term storage for biological control have generally included freezing cells in suspension, such as in buffer, or freeze-drying with osmoprotectants, or drying cells with osmoprotectants then keeping them in cold storage 4° C. (see e.g., Crowe, J. H., et al., (1987) *Biochemistry Journal,* 242, 1-10; Crowe, J. H., et al., (1988) *Biochim Biophys Acta,* 947, 367-384; Spadaro, D., et al., (2010) *Canadian Journal of Microbiology,* 56(10), 809-815). However, the lowest cost industrial drying process for preparing heat labile materials for stable storage is spray drying (see e.g., Yanez-Mendizabal, V., et al. (2012) *Biotechnology Letters,* 34(4), 729-735; Yánez-Mendizábal, V., et al. (2102) *Journal of Applied Microbiology,* 112(5), 954-965), so the design of the engineered mutagenesis protocol herein described to select for strains able to survive rapid air drying in droplets of spent broth without osmoprotection was a key point of strain improvement for future successful BCA manufacturing. Additionally, the results of the prior seven-strain survey indicated that cell survival at 25° C. storage was generally much poorer than at 4° C. Thus, the engineered mutagenesis protocol would be selecting for cells able to survive lower cost non-refrigerated conditions.

In addition to promoting the enrichment of strains more fit for successful manufacturing practices, the engineered mutagenesis strategies herein applied, also had the overall benefit of increasing the incidence and speed of cell death processes due to the applied spartan conditions of rehydration and cultivation (MG medium), drying, and storage. This scenario is expected to make the enrichment of desired individuals a more efficient process, reducing the time to achieve desired strain improvements. Significant improvement of the strain *Pseudomonas* sp. S11P12 (Table 2) was observed after only about 20 weeks (<6 months) of conducting the engineered mutagenesis process (FIG. 1). As an additional feature supporting efficiency, the engineered mutagenesis process was designed to be applied in microplates, such that the entire process could be automated with current technologies, thus making the path to desiccation-tolerance quickly traversable for *Pseudomonas* and other genera of microorganisms previously difficult to store in dry form.

In previous studies, the use of the microplate droplet drying bioassay was shown to have strong potential as a high-throughput primary screening and optimization tool because it is efficient and automatable, as well as being very sensitive to process variables that impact BCA drying and storage survival. The tool utilized the rate of culture absorbance change read with a plate reader to monitor the rate of cell regrowth from dried cell droplets in microplate wells, which was a sensitive measure of surviving cell activity as a function of both viable cell number and physiological activity. Such a screening tool was used to rapidly optimize a chain of production, formulation, storage and reconstitution conditions required to commercialize numerous bacterial agents showing promise for biological control. In the engineered mutagenesis application described herein, this basic technique was again applied to evaluate strain improvement as a result of the mutagenesis process. The droplet drying process element may also serve as an automatable selection strategy for directing strain improvement. In this instance, instead of optimizing manufacturing conditions to support the ability of a strain to survive dry storage, the objective could be to improve the strain resilience to accommodate lowest cost manufacturing process conditions and materials.

Retaining Key Bioactivity Phenotypes not Explicitly Enriched by the Engineered Mutagenesis Process. All three of the strains subjected to the engineered mutagenesis process of FIG. 1 have previously been documented to produce multiple antifungal antibiotics (see e.g., Burkhead, K. D., et al. (1995) *Soil Biology and Biochemistry*, 27(12), 1611-1616). Such metabolites may be an important mode of action allowing biocontrol agents to successfully compete against fungal pathogens at wound sites on potato surfaces. The antibiotic production phenotype would be a key feature to retain in improved BCA strains amenable to low-cost manufacturing. However, the engineered mutagenesis process herein applied did not exert a direct selection pressure to enrich the mutating populations for individuals having antifungal bioactivity. For this reason, it was necessary to evaluate putative desiccation tolerant isolates for their ability to suppress *Fusarium* dry rot of potatoes using the wounded potato bioassay. Additionally, the indicator plating techniques aided timely viewing of morphological and metabolic changes that occurred during mutagenesis. For example, fluorescence on KMB was expected of all three strains, and was a convenient check for retention of iron-sequestering fluorescent siderophores beneficial to biological control by competitive exclusion of other micro-organisms. Growth on histidine in the MDL medium with histidine as a sole carbon source and tetrazolium red was used to visually monitor relative shifts in colony morphologies that might indicate an unwanted population drift away from histidine utilization for strain P22Y05, a feature useful in selective dilution plating of this strain in co-culture with S11P12 and S22T04 which cannot use histidine as a sole carbon source. Plating mutating populations of all three strain lines onto 1/5 TSA with tetrazolium red was also useful to check colony morphologies, especially within the S11P12 strain line for visualization of marginalan polysaccharide production, which generally results in a unique pattern of concentric red circles on the slimy colony. Strain S11P12 produces the desiccation protective polysaccharide marginalan in strongly aerated fermentors. The indicator plating media provided a measure of quality control to spot infection of the engineered mutagenesis process with contaminants, although 16S rRNA gene sequences were relied upon for final confirmation of improved isolate species.

Broader Impact of the Engineered Mutagenesis Technique on a Developing Market for New Biologicals. As a broader impact of this invention, the high throughput strain development tool presented herein may support products for biological control and promotion of plant health as a rapidly expanding opportunity for industrial development. Several *Pseudomonas* species have been sequenced and many molecular tools are available for manipulation of strains for use in the field of BCAs. However, commercial application has been limited by low resilience to drying and storage and amenability to industrial production using lowest cost processes and materials even though they are a significant, largely untapped reservoir of new products for plant health that are consistent with preserving the environment and minimizing mechanisms of anti-microbial resistance that threaten current agricultural and medical tools for plant and human health. Consequently, commercial interest in BCAs thus far has been most often restricted to spore-forming microorganisms which are natively resistant to drying or which contain storage-stable endotoxins not requiring a viable cell for successful application, such as *Bacillus* sp., for example *B. thuringiensis*, or *B. subtilis*. Strain improvement tools, such as the engineered mutagenesis strategy presented herein (FIG. 1), support the development of *Pseudomonas* spp. and other non-spore-forming microorganisms as biological control products.

Example: Switchgrass Hydrolyzate Tolerance

Cultivations and Monitoring. Wild type *Pseudomonas fluorescens* strains S11P12, S22T04, and P22Y05 and engineered strains P12-42d-D9, T04-126d-F4, and Y05-214d-4 were stored long term at −80° C. in 10% glycerol stocks. The glycerol stocks were used to inoculate several 1/5 TSA plates (6 g/L Tryptic Soy Broth, 15 g/L agar) which were incubated 2-3 days at 25° C. and then refrigerated. Test culture inocula were from 10-mL SDCL medium pre-cultures in 50-mL flasks inoculated by loop from plates and incubated 24 hrs at 25° C., 300 rpm (1" stroke) prior to use. The 24-hr unwashed cells were concentrated by centrifugation (10 min, 7000 rpm) to an optical density of $A_{620}$ 50 and used to inoculate test culture wells to an initial optical density of 0.5. Each test culture was grown on switchgrass hydrolyzate (SGH) of various strengths as reflected by total glucose and xylose concentrations at 10, 15, or 20 g/L. Isolates were grown in duplicate 10-mL cultures in 50-mL flasks on SGH with buffer provided at 2 g/L each of $K_2HPO_4$ and $KH_2PO_4$ to maintain pH in the 6-8 range and amino acids supplied to give a 23.5:1 C:N ratio. For example, DIFCO Vitamin Assay (i.e., vitamin free) Casamino Acids was supplied in this study. Culture flasks were incubated at 25° C. and 300 rpm and sampled initially and later at 16, 24, and 41 h. Culture samples were plated for viable cell concentration, evaluated for cell growth by optical density using an Evolution 60s spectrophotometer (620 nm, 1 cm pathlength), checked for pH, and then submitted to high performance liquid chromatography analysis of sugars and inhibitors using BIORAD HPX87H and BIORAD HPX87P carbohydrate analysis columns as described previously (see e.g., Slininger P. J., et al. (2015) *Biotechnology for Biofuels*. 8(60): 1-27; Slininger P. J., et al., (2016) *Biotechnology and Bioengineering* 113:1676-1690; U.S. Pat. No. 9,297,027).

Complete SDCL at 23.5:1 C:N Ratio. The ingredients were as follows: 4 g/L $K_2HPO_4$, 4 g/L $KH_2PO_4$ buffers; 0.01 g/L $FeSO_4(7H_2O)$, 0.1 g/L $MgSO_4(7H_2O)$, 0.0044 g/L $ZnSO_4(7H_2O)$, 0.01 g/L NaCl, 0.011 g/L $CaCl_2(2H_2O)$, 0.01 g/L $MnCl_2(4H_2O)$, 0.002 g/L $(NH_4)_6Mo_7O_{24}(4H_2O)$, 0.0024 g/L $H_3BO_3$, 0.05 g/L EDTA trace minerals; 0.01 g/L each of adenine, cytosine, guanine, uracil, and thymine purines and pyrmidines; 0.5 mg/L each of thiamine, riboflavin, calcium pantothenate, niacin, pyridoxamine, and thioctic acid vitamins; 0.05 mg/L each of folic acid, biotin and vitamin $B_{12}$ vitamins; 15 g/L Vitamin Free Casamino Acids, 0.6 g/L cysteine, and 0.15 g/L tryptophan to provide 0.042 M N nitrogen; 10 g/L glucose carbon source. Initial pH was adjusted to 6.8-7.0.

Preparation of SGH. Switchgrass hydrolyzates were prepared from Kanlow N1 baled post-frost from Mead, Nebr., USA, that was milled to pass through a 2 mm screen. Switchgrass was pretreated at the 20% solids level by mixing 20 g dry weight of biomass with 80 mLs of 0.936% (v/v) sulfuric acid solution and 0.3 g PLURONIC F-268 high molecular weight polyoxyalkylene ether. Each of 12 closed stainless-steel vessels was loaded with reactants and mounted in a MATHIS LABOMAT IR Dyer Oven where they were rotated at 50 rpm (1 min right then 1 min left) and heated to 160° C., held for 15 min, and then cooled at 40° C. After pretreatment, the product was adjusted to pH 4.5 by adding 7.14 mL of 15% $Ca(OH)_2$ solution and 4.5 mL of 1 M citric acid buffer directly into each vessel and then tumbling 15 min in the LABOMAT IR Dyer Oven. Pretreatment hydrolyzates were transferred to 250 mL pyrex bottles for saccharification. To each bottle, 2.7-mL of CTEC and 0.5-mL of HTEC enzymes for conversion of biomass into fuel and bio-chemicals (Novozyme) were added. Tightly capped bottles were incubated ~72-h at 50° C. and 175 rpm. Resulting hydrolyzates were sterile filtered through 0.2 μm NALGENE filter units (Nalge Nunc International; Rochester, N.Y.) and refrigerated at 4° C. until use.

Figure 5A:
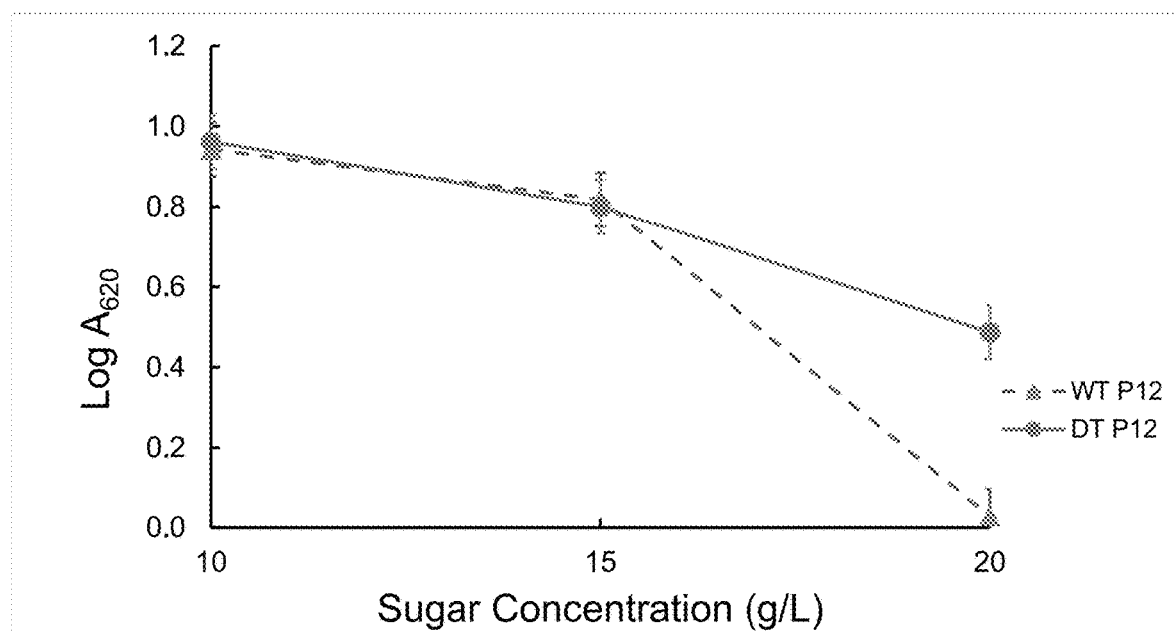
FIG. 5A to 5F show tolerance levels against switchgrass hydrolysate of parent strains relative to novel engineered strains.
Figure 5B:
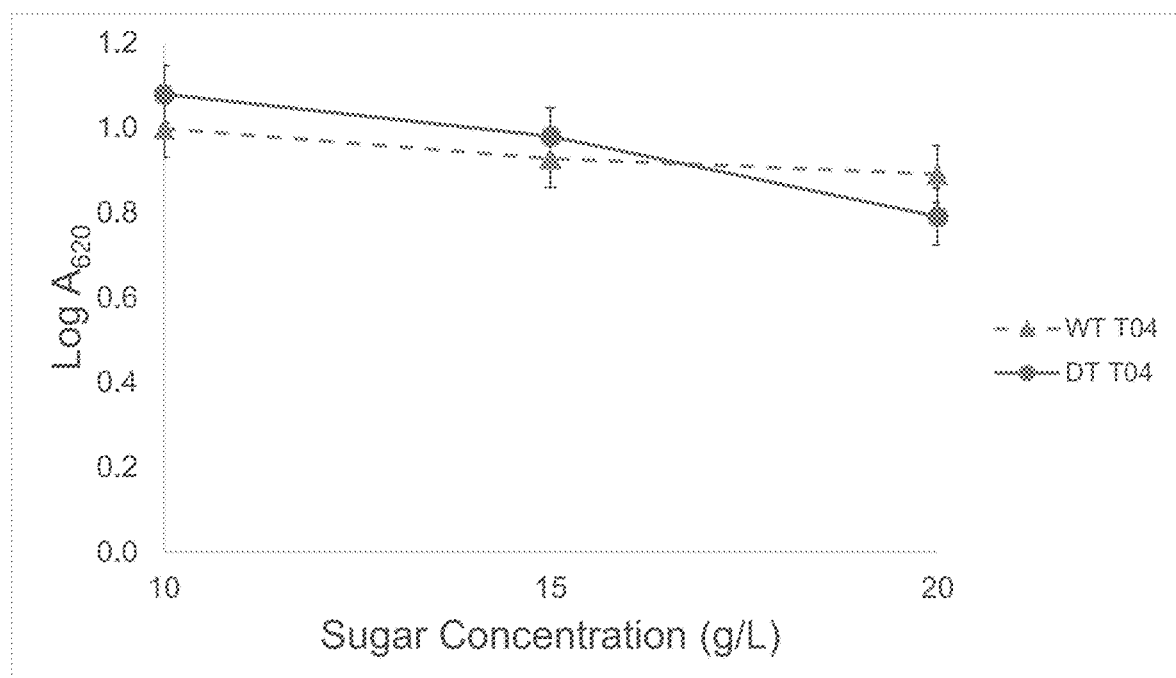
Figure 5C:
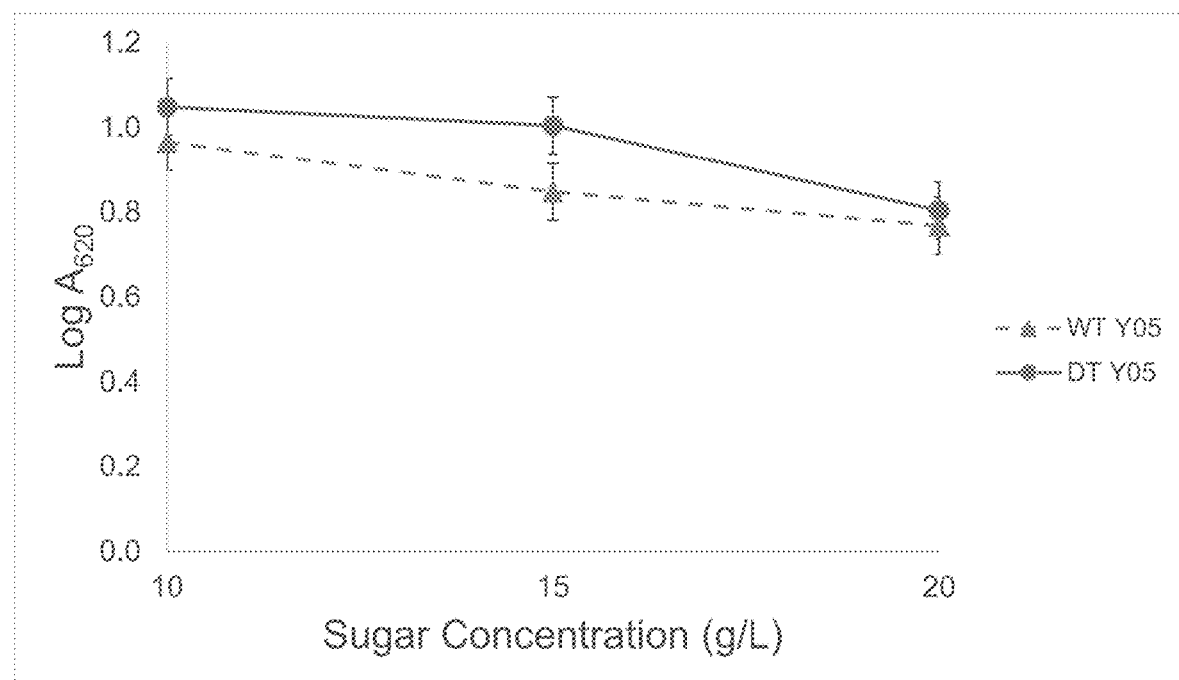
Figure 5D:
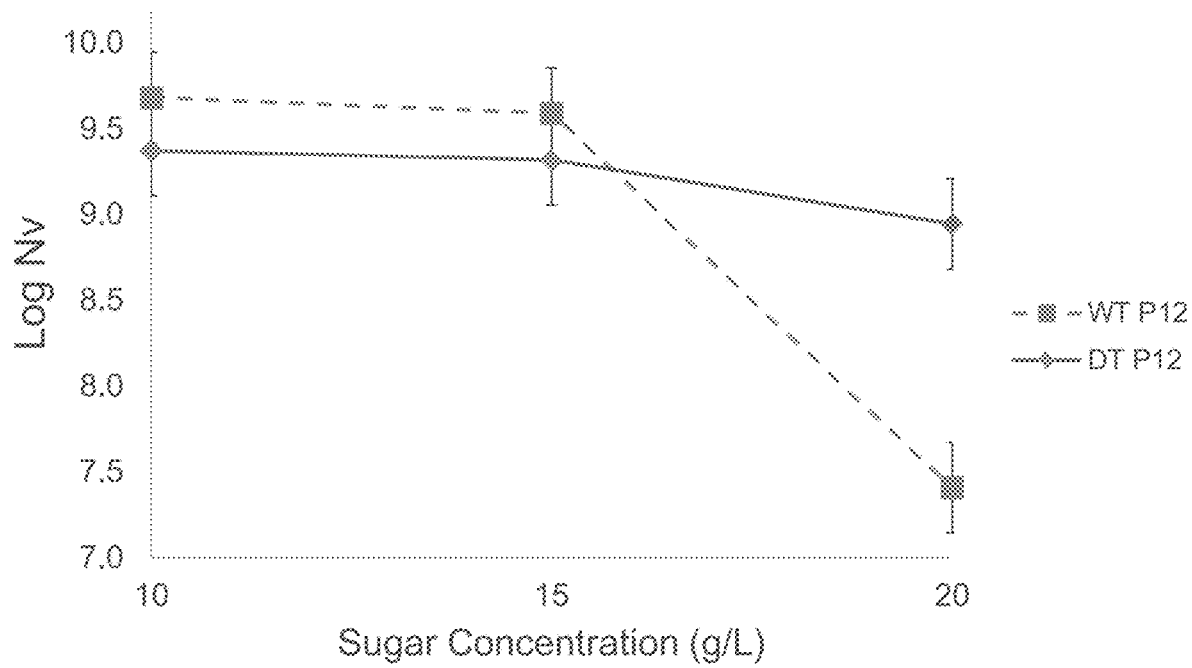
Figure 5E:
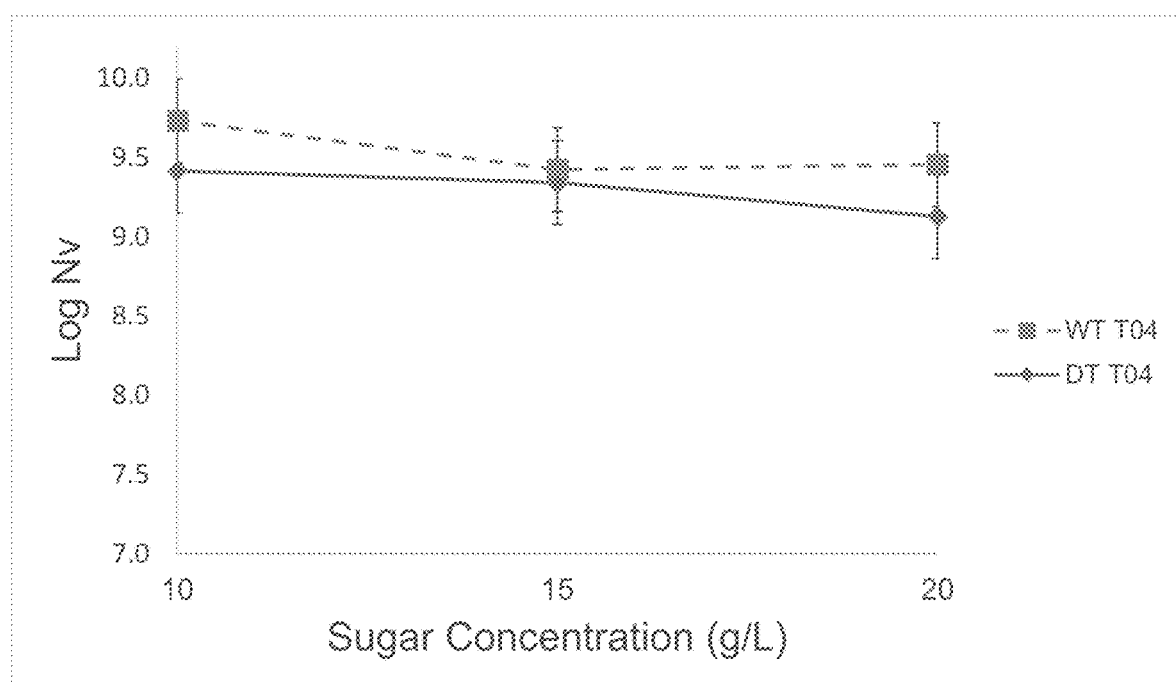
Figure 5F:
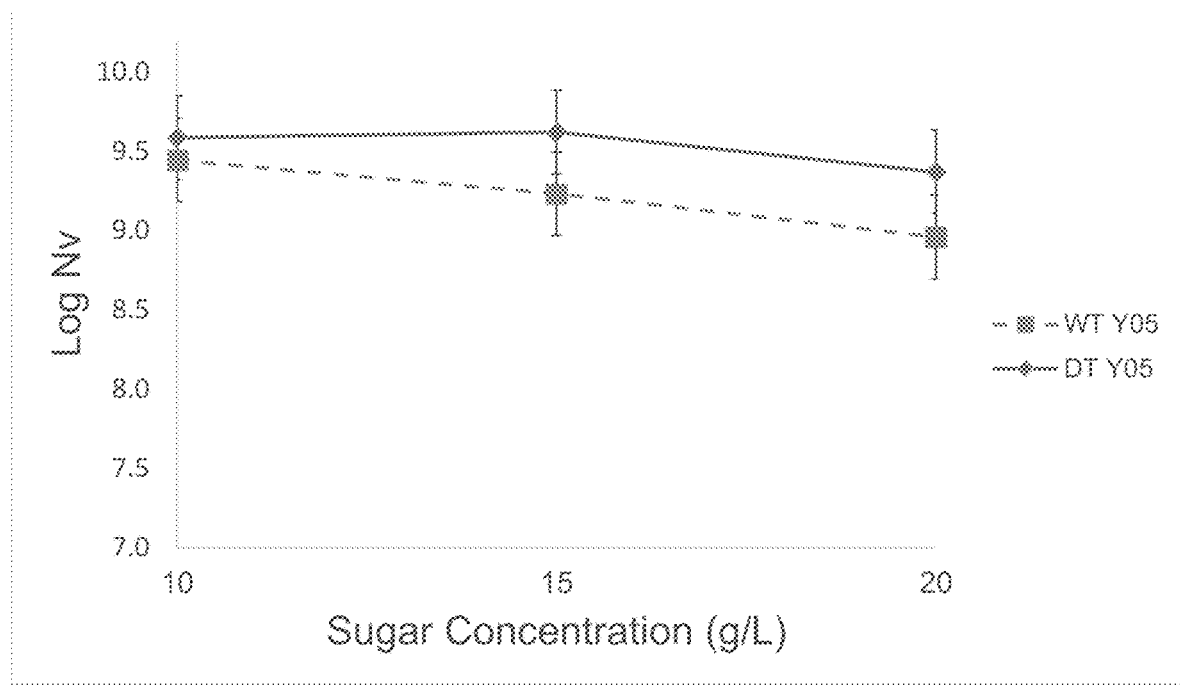

Results and Discussion. A three-way analysis of variance of the log biomass production (Log $A_{620}$) as a function of *Pseudomonas* strain type (wild versus desiccation tolerant) x parent *Pseudomonas* strain (S11P12, S22T04, or P22Y05) x sugar concentration (10, 15, or 20 g/L) showed significant effects ($P<0.05$) for type, strain, and sugar as well as the 2-way interaction strain x sugar and the 3-way interaction type x strain x sugar. FIG. 5A to 5C show these relationships. A three-way analysis of variance of the log viable cell production (Log $N_v$, cfu/mL) as a function of strain type (wild versus desiccation tolerant) x parent strain (S11P12, S22T04, or P22Y05) x sugar concentration (10, 15, or 20 g/L) showed significant effects ($P<0.05$) for strain and sugar as well as the 2-way interaction strain x sugar and the 3-way interaction type x strain x sugar. FIG. 5D to 5F show these relationships.

The data show that cell biomass and viable cell productions were overall at higher levels for two of the three desiccation tolerant (DT) biocontrol strains compared with their wild type (WT) parent strains, especially when the hydrolyzate strength was increased to provide 20 g/L sugars. As hydrolyzate concentration is increased to provide from 10 to 20 g/L sugar concentration, the microbial inhibitors (furfural and hydroxymethylfurfural) are also increased. As a result, the *Pseudomonas* strains would be expected to be less tolerant; however, two (S11P12 DT and P22Y05 DT) of three desiccation tolerant strains tested were surprisingly more resistant to the inhibitory levels of SGH than were their respective parent strains. Especially dry tolerant S11P12 showed the most significant improvement compared to its parent ($P<0.001$) with respect to both Log $N_v$ and Log $A_{620}$.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety, including any materials cited within such referenced materials. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

---

The claimed invention is:

1. A novel strain having identifying characteristics of being capable of surviving rapid air drying in droplets of spent broth without osmoprotection, and being capable of surviving non-refrigerated storage conditions, wherein the novel strain is produced from a parent strain of *Pseudomonas fluorescens*, and the novel strain is selected from the group consisting of: *Agricultural Research* Service (ARS) Culture Collection Patent Deposit Accession Numbers NRRL B-67667; NRRL B-67668; NRRL B-67669; NRRL B-67670; NRRL B-67671; NRRL B-67672; NRRL B-67673; NRRL B-67674; NRRL B-67675; and combinations or cocultures thereof.

2. The novel strain of claim 1, wherein the identifying characteristics further include viable cell yield during growth, efficacy in suppression of dry rot disease, and cell growth recovery after dry storage.

3. The novel strain of claim 1, wherein the identifying characteristics further include tolerance to switchgrass hydrolysate.

4. The novel strain of claim 1, wherein the identifying characteristics further include growth and bioefficacy phenotypes that are at least about 1.6 times more active after rehydration from partially or fully desiccated conditions as compared to the parent strain of *Pseudomonas fluorescens*.

5. The novel strain of claim 1, wherein the identifying characteristics further include growth and bioefficacy phenotypes that are from about 1.6 to about 6 times more active after rehydration from partially or fully desiccated conditions as compared to the parent strain of *Pseudomonas fluorescens*.

6. The novel strain of claim 1, wherein the identifying characteristics further include enhanced capability and tolerance to withstand long-term storage; enhanced capability and tolerance to withstand partially or fully desiccated storage, while maintaining growth and bioefficacy phenotypes when rehydrated; enhanced growth and bioefficacy phenotypes; and combinations thereof, wherein the enhancements are when compared to the parent strain.

7. A composition comprising the novel strain of claim 1.

8. The composition of claim 7, which is at least partially dehydrated and has less than about 30% water content.

9. The composition of claim 7, which is at least partially dehydrated and has less than about 15% water content.

10. A method of generating a novel microbial strain of claim 1 having identifying characteristics of being capable of surviving rapid air drying in droplets of spent broth without osmoprotection, and being capable of surviving non-refrigerated storage conditions, the method comprising: (a) culturing a parent strain of the novel microbial strain in a first medium for a time sufficient to achieve a predetermined culture density and create a base culture; (b) passaging the base culture by drawing one or more samples from the base culture to create at least one passaged sample; (c) optionally pelletizing the at least one passaged sample and suspending each passaged sample separately in a second medium to create a series of passaged samples; (d) subjecting the series of passaged samples to at least one stress condition to create a series of stressed samples; (e) measuring at least one characteristic of the series of stressed samples to create at least one measured characteristic; and (f) determining whether the measured characteristic is superior to the same characteristic of the parent strain to select at least one novel mutant strain from the series of stressed samples; further comprising replacing the parent strain in step (a) with one or more of the selected mutant strains from step (f) and repeating steps (a) to (f).

11. The method of claim 10, wherein the measured characteristic is selected from the group consisting of: enhanced capability and tolerance to withstand long-term storage; enhanced capability to tolerate at least partially desiccated storage, while maintaining growth and bioefficacy phenotypes when rehydrated; enhanced growth and bioefficacy phenotypes; and combinations thereof.

12. The method of claim 10, wherein the measured characteristic includes enhanced capability to tolerate at least partially desiccated storage, while maintaining growth and bioefficacy phenotypes when rehydrated.

13. The method of claim 10, wherein the parent strain is a *Pseudomonas fluorescens* strain and selected from the group consisting of: strain P22:Y:05, having ARS Culture Collection Patent Deposit Accession Number NRRL B-21053; strain S11:P:12, having ARS Culture Collection Patent Deposit Accession Number NRRL B-21133; strain S22:T:04 having ARS Culture Collection Patent Deposit Accession Number NRRL B-21102; and combinations or cocultures thereof.

14. The method of claim 10, further comprising preparing a dried culture from the novel mutant strain.

15. A method of treating an agricultural product with a novel strain having identifying characteristics of being capable of surviving rapid air drying in droplets of spent broth without osmoprotection, and being capable of surviving non-refrigerated storage conditions, wherein the novel strain is selected from the group consisting of: *Agricultural Research* Service (ARS) Culture Collection Patent Deposit Accession Numbers NRRL B-67667; NRRL B-67668; NRRL B-67669; NRRL B-67670; NRRL B-67671; NRRL B-67672; NRRL B-67673; NRRL B-67674; NRRL B-67675; and combinations or cocultures thereof, the method comprising applying the novel strain to the agricultural product; wherein the agricultural product is any type of potato.

16. The method of claim 15, further comprising: (a) rehydrating a dehydrated composition comprising the novel strain to produce a rehydrated novel strain and (b) applying the rehydrated novel strain to the agricultural product.

17. The method of claim 16, wherein the dehydrated composition contains no more than about 30% water based on weight.

18. The method of claim 16, further comprising applying the rehydrated novel strain to the agricultural product to control dry rot-inducing fungi.

19. A kit for carrying out the method of claim 15, the kit comprising a first container means containing the novel strain; optionally other container means comprising a solution, diluent, or applicator for the novel strain; and written information including procedures for applying the novel strain to the agricultural product.

\* \* \* \* \*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
agagtttgat cctggctcag                                         20

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized
```

```
<400> SEQUENCE: 2
ggttaccttg ttacgactt                                                   19
```